United States Patent
Armitage et al.

(10) Patent No.: US 10,745,404 B2
(45) Date of Patent: Aug. 18, 2020

(54) PROCESS FOR THE SYNTHESIS OF E1 ACTIVATING ENZYME INHIBITORS

(71) Applicant: Millennium Pharmaceuticals, Inc., Cambridge, MA (US)

(72) Inventors: Ian Armitage, Medford, MA (US); Eric L. Elliott, Brighton, MA (US); Marianne Langston, North Andover, MA (US); Steven P. Langston, North Andover, MA (US); Quentin J. McCubbin, Belmont, MA (US); Hiro Mizutani, Cambridge, MA (US); Matthew Stirling, Boston, MA (US); Lei Zhu, Bedford, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/713,293

(22) Filed: Sep. 22, 2017

(65) Prior Publication Data
US 2018/0079755 A1 Mar. 22, 2018

Related U.S. Application Data

(62) Division of application No. 14/552,883, filed on Nov. 25, 2014, now Pat. No. 9,802,938, which is a division of application No. 12/221,399, filed on Aug. 1, 2008, now Pat. No. 8,933,225.

(60) Provisional application No. 61/062,378, filed on Jan. 25, 2008, provisional application No. 60/963,008, filed on Aug. 2, 2007.

(51) Int. Cl.
| | | |
|---|---|---|
| *C07D 487/04* | (2006.01) | |
| *A61K 31/519* | (2006.01) | |
| *A61P 35/00* | (2006.01) | |
| *C07C 215/44* | (2006.01) | |
| *C07C 217/52* | (2006.01) | |
| *C07C 219/24* | (2006.01) | |
| *C07D 211/96* | (2006.01) | |
| *C07D 213/89* | (2006.01) | |
| *C07D 241/50* | (2006.01) | |
| *C07D 295/22* | (2006.01) | |
| *C07D 471/08* | (2006.01) | |
| *C07C 315/04* | (2006.01) | |
| *C07C 317/50* | (2006.01) | |
| *C07D 305/08* | (2006.01) | |

(52) U.S. Cl.
CPC .......... *C07D 487/04* (2013.01); *A61K 31/519* (2013.01); *A61P 35/00* (2018.01); *C07C 215/44* (2013.01); *C07C 217/52* (2013.01); *C07C 219/24* (2013.01); *C07C 315/04* (2013.01); *C07C 317/50* (2013.01); *C07D 211/96* (2013.01); *C07D 213/89* (2013.01); *C07D 241/50* (2013.01); *C07D 295/22* (2013.01); *C07D 305/08* (2013.01); *C07D 471/08* (2013.01); *C07C 2601/08* (2017.05); *Y02P 20/55* (2015.11)

(58) Field of Classification Search
CPC .......................... C07D 487/04; A61K 31/519
See application file for complete search history.

(56) References Cited

U.S. PATENT DOCUMENTS

| | | |
|---|---|---|
| 4,081,455 A | 3/1978 | Kuhla |
| 4,138,433 A | 2/1979 | Kleiner et al. |
| 4,803,272 A | 2/1989 | Anton et al. |
| 4,927,830 A | 5/1990 | Townsend et al. |
| 5,534,535 A | 7/1996 | Townsend et al. |
| 5,912,356 A | 6/1999 | Townsend et al. |
| 6,379,552 B1 | 4/2002 | Kitagawa et al. |
| 6,562,861 B1 | 5/2003 | Babu et al. |
| 6,878,716 B1 | 4/2005 | Castelhano et al. |
| 7,067,683 B2 | 6/2006 | Geisler et al. |
| 7,951,810 B2 | 5/2011 | Critchley et al. |
| 8,008,307 B2 | 8/2011 | Claiborne et al. |
| 8,933,225 B2 | 1/2015 | Armitage et al. |
| 9,802,938 B2 | 10/2017 | Armitage et al. |
| 2006/0189636 A1 | 8/2006 | Critchley et al. |
| 2007/0191293 A1 | 8/2007 | Langston et al. |
| 2008/0051404 A1 | 2/2008 | Claiborne et al. |
| 2008/0096922 A1 | 4/2008 | Ban et al. |
| 2011/0136834 A1 | 1/2011 | Critchley et al. |
| 2011/0021544 A1 | 6/2011 | Armitage et al. |

FOREIGN PATENT DOCUMENTS

| | | |
|---|---|---|
| EP | 1736467 | 12/2006 |
| WO | WO 93/17020 | 9/1993 |

(Continued)

OTHER PUBLICATIONS

Anderson, M. W., et al., "The Synthesis of Modified D- and L-Anhydrohexitol Nucleosides," *Tetrahedron Lett.*, vol. 37(45): 8147-8150 (1996).

(Continued)

*Primary Examiner* — Susanna Moore
(74) *Attorney, Agent, or Firm* — Sterne, Kessler, Goldstein & Fox, P.L.L.C.

(57) ABSTRACT

The present invention provides processes and synthetic intermediate (Ia) for the synthesis of 4-substituted ((1S, 2S, 4R)-2-hydroxy-4-{7H-pyrrolo[2,3-d]pyrimidin-7-yl}cyclopentyl)methyl sulfamates. These sulfamate compounds are E1 activating enzyme inhibitors, and are useful for the treatment of disorders of cell proliferation, particularly cancer, and other disorders associated with E1 activity.

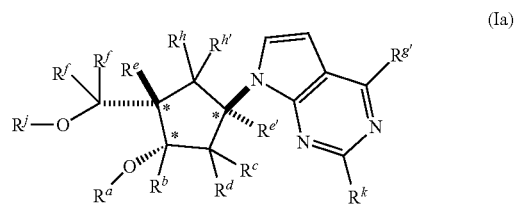

(Ia)

7 Claims, No Drawings

(56) References Cited

FOREIGN PATENT DOCUMENTS

| | | |
|---|---|---|
| WO | WO 93/18009 A1 | 9/1993 |
| WO | WO 96/07646 A1 | 3/1996 |
| WO | WO 99/33781 A1 | 7/1999 |
| WO | WO 00/58500 A1 | 10/2000 |
| WO | WO 01/36398 | 5/2001 |
| WO | WO 01/42255 | 6/2001 |
| WO | WO 01/43731 A2 | 6/2001 |
| WO | WO 03/053992 | 7/2003 |
| WO | WO 03/105770 | 12/2003 |
| WO | WO 03/106477 | 12/2003 |
| WO | WO 2004/041799 A1 | 5/2004 |
| WO | WO 2005/007085 A2 | 1/2005 |
| WO | WO 2005/039486 A2 | 5/2005 |
| WO | WO 2005/095357 A2 | 10/2005 |
| WO | WO 2005/097738 A1 | 10/2005 |
| WO | WO 2006/084281 A1 | 8/2006 |
| WO | WO 2007/092213 A2 | 8/2007 |
| WO | WO 2008/019124 A1 | 2/2008 |

OTHER PUBLICATIONS

Armitage, I., "Process Development Towards a Practical Synthesis of investigational NEDD8-Activating Enzyme Inhibitior, MLN4924," Presented Oct. 19, 2011 at AMRI Chemical Development Symposium, Albany, New York.
Atkins, Jr., G. M., et al., "Synthesis and Reactions of N-Sulfonylamines," *Journal of American Chemical Society*, vol. 94(17): 6135-6141 (1972).
Bannister, R., et al., "Process Research and Development for the Production of intermediates for the Synthesis of Carbocyclic Nucleosides," *Organic Process Research & Development*, vol. 1(6): 415-419 (1997).
Benltifia, M., et al., "Synthesis and evaluation of sulfamide-type indolizidines as glycosidase inhibitors," *Bioorganic & Medicinal Chemistry Letters*, vol. 18(9): 2805-2808 (2008).
Bisagni, E., et al., "New heterocyclic rearrangement: transformation of 1-substituted 4-(alkylamino) 1H-pyrrolo[3,2-c]pyridines into 1-Substituted 4-(Alkylamino)-1H-pyrrolo[2,3-b]pyridiries (5-Aza- to 7-Azaindoles)," *Journal of Organic Chemistry*, vol. 47(8): 1500-1503 (1982).
Bray, B. L., et al., "Improved Procedures for the Preparation of (+)-(1R, 2S, 4R)-4-Amino-2-Hydroxy-1-Hydroxymethyl Cyclooentane." *Tetrahedron Letters*, vol. 36(25): 4483-4486 (1995).
Burgess, E. M., et al., "Thermal reactions of alkyl N-Carbomethoxysulfamate Esters," *Journal of Organic Chemistry*, vol. 38(1): 26-31 (1973).
Chen, X., et al., "Chemoenzymatic Synthesis of (−)-Carbocyclic 7-Deazaoxetanocin G," *Tetrahedron Lett.*, vol. 33(17): 2249-2252 (1992).
Clark, M. P., et al., "Development of new pyrrolopyrimidine-based inhibitors of Janus kinase 3 (JAK3)," *Bioorganic & Medicinal Chemistry Letters*, vol. 17(5): 1250-1253 (2007).
Cristalli, G., et al., "Adenosine Deaminase Inhibitors. Synthesis and Biological Activities of Deaza Analogs of erythro-9-(2-Hydroxy-3-nonyl)adenine," *Journal of Medicinal Chemistry*, vol. 31(2): 390-393 (1988).
Csuk, R., et al., "Biocatalytical Transformations. VI. The 4-Acetamido-cyclopent-2-ene Carboxylate Route Revisited: Synthesis of (+)- and (−)-Aristeromycin," *Tetrahedron*, vol. 51(20): 5789-5798 (1995).
Dominguez, B. M., et al., "2-Azabicyclo[2.2.1]hept-5-en-3-one Epoxide: A Versatile Intermediate for the Synthesis of Cyclopentyl Carbocyclic 2-Deoxy-, 3-Deoxy- & Ara-Ribonucleoside Analogues," *Tetrahedron Letters*, vol. 40(31): 5783-5786 (1999).
European Examination Report dated Jun. 7, 2010 in European Patent Application 08832973.5 which corresponds to U.S. Appl. No. 12/221,399.
European Search Report European Patent Application No. 12 17 2363, dated Nov. 21, 2012.
European Search Report for European Patent Application No. 12 17 2363, dated Mar. 8, 2013.
European Search Report for European Patent Application No. 12 17 2364, dated Nov. 14, 2012.
European Search Report for European Patent Application No. 12 17 2365, dated Nov. 16, 2012.
Gosselin, G., et al., "A Short and novel synthesis of carbocyclic nucleosides and 4'-epi-carbocyclic nucleosides from 2-cyclopenten-1-ones," *Tetrahedron*, vol. 62(5): 906-914 (2006).
Gudmundsson, K. S., et al., "Phosphoramidate Protides of Carbocyclic 2',3'-Dideoxy-2',3'-Didehydro-7-Deazaadenosine with Potent Activity Against HIV and HBV," *Nucleosides, Nucleotides and Nucleic Acids*, vol. 23(12): 1929-1938 (2004).
Ho, J. Z. et al., "Enantiospecific Synthesis of Carbapentostatins," *Journal of Organic Chemistry*, vol. 68(1):109-114 (2002).
Holy, A., "Nucleic acid components and their analogs. CLXXXI. Preperation of Substituted (±)-5t-hydroxymethyl-3t-aminocyclopentane-1r,2c-diol Derivatives Related to Carbocyclic Ribnucleoside Analogs," Chemical Abstracts Service, Database Accession No. 1976:180520.
Holy, A., "Preparation of substituted (±)-5t-hydroxymethyl-3t-aminocyclopentane-1r,2c-diol derivatives related to carbocyclic ribonucleoside analogues," *Collection of Czechoslovak Chemical Communication*, vol. 41(2): . 647-665 (1976).
Hurtley, S. (ed.), "Chemistry: One After Another," *Science*, vol. 310: 409 (2005).
International Search Report with Written Opinion dated Feb. 2, 2009 from PCT/US08/009338 corresponding to U.S. Appl. No. 12/221,399.
Jäger, U., et al., "Zur Synthese Perfluorierter Sulfimide, $R_fN=SO_2$, und deren Stabilisierung durch tertiäre Amine," *Chem, Ber*. vol. 120, pp. 1191-1195 (1987).
Kam, B. L., et al., "Carbocyclic Sugar Amines: Synthesis and Stereochemistry of Racemic α- and β-Carbocyclic Ribofuranosylamine, Carbocyclic Lyxofuranosyiamine, and Related Compounds," *Journal of Organic Chemistry*, vol. 46( 16): 3268-3272 (1981).
Katagiri, N., et al., "A Highly Efficient Synthesis of the Antiviral Agent (+)-Cyclaradine Involving the Regloselective Cleavage of Epoxide by Neighboring Participation," *Tetrahedron Letters*, vol. 38(11): 1961-1964 (1997).
Kelley, J. L., et al., "Synthesis and Anticonvulsant Activity of N-benzylpyrrolo[2,3-d]-, pyrazolo[3,4-d]-, and -triazolo[4,5-d]pyrimidines: Imidazole Ring-Modified Analogues of 9-(2-Fluorobenzyl)-6-(methylamino)-9H-purine," *Journal of Medicinal Chemistry*, vol. 38,(19): 3884-3888 (1995).
Kudoh, T., et al., "Synthesis of Stable and Cell-type Selective Analogues of Cyclic ADP-Ribose, $Ca^{2+}$-Mobilizing Second Messenger. Structure-Activity Relationship of the N-Ribose Moiety," *Journal of American Chemical Society*, vol. 127(24): 8846-8855 (2005).
Legraverend, M., et al.,"(±)-2-amino-3,4-dihydro-7[2,3-dihydroxy-4-(hydroxymethyl)-1—cyclopentyl 7H-pyrrolo[2,3-d]pyrimidin-4-ones: New Carbocyclic Analogues of 7-Deazaguanosine with Antiviral Activity," *Journal of Medicinal Chemistry*, vol. 28: 1477-1480 (1985).
Leisch, H., et al., "New Options for the Reactivity of the Burgess Reagent with Epoxides in Both Racemic and Chiral Auxiliary Modes13 Structural and Mechanistic Revisions, Computational Studies, and Application to Synthesis," *European Journal of Organic Chemistry*, vol. 17: 2806-2819 (2009).
Marco-Contelles, J., et al., "Asymmetric Synthesis of Cyclopentylamine Derivatives, Intermediates for Carbocyclic Nucleoside Synthesis. Carbocyclization of 2-Amino-5-hexenyl Radicals," *Tetrahedron Letters*, vol. 35(34): 6361-6364 (1994).
Mineno, T., et al., "Stereoselective total synthesis of racemic BCX-1812 (RWJ-270201) for the development of neuraminidase inhibitors as anti-influenza agents,"*Journal of Organic Chemistry*, vol. 68, No. 17 (2003) pp. 6591-5596.
Montgomery, J. A., et al. "Analogs of Tubercidin," *Journal of Medicinal Chemistry*, vol. 10(4): 665-667 (1967).

(56) References Cited

OTHER PUBLICATIONS

Nicolaou, K. C., et al., "New Uses for the Burgess Regent in Chemical Synthesis: Methods for the Facile and Steroselective Formation of Sulfamidates, Glycosylamines, and Sulfamides," *Chemistry—A European Journal*, vol. 10(22): 5581-5606 (2004).
Okada, M., et al., "Efficient general method for sulfamoylation of a hydroxyl group," *Tetrahedron Letters*, vol. 41(36): 7047-7051 (2000).
Ötvös, L., et al., "The First Stereospecific Synthesis of (+)-(1R,2S,4R)-4-Amino-2-hydroxy-l-cyclopentanemethanol and (+)-Carbocyclic Thymidine," *Tetrahedron Lett.*, vol. 28(50): 6381-6384 (1987).
Pecquet, P., et al., "Synthesis of New Carbocyclic Analogues of Oxetanocin A and Oxetanocin G," *Heterocycles*, vol. 34(4): 739-745 (1992).
Pudlo, J. S., et al., "Synthesis and Antiviral Activity of Certain 4- and 4,5-Disubstituted 7-[(2-Hydroxyethoxy) methyl]pyrrolo[2,3-d]pyrimidines," *Journal of Medicinal Chemistry*, vol. 31: 2086-2092 (1988).
Rapoport, H., et al., "An Efficient Procedure for the Preparation of (1S,3R)- and (1S,3S)-1-Amino-3 (hydroxymethyl)cyclopentanes," *Chemical & Pharmaceutical Bulletin*, vol. 51(10): 1153-1156 (2003).
Regaïnia, Z., et al., "Synthesis of 1,2,5-Thiadiazolidines 1, 1-dioxides (*Cyclosulfamides*) Starting from Amino Acids and Chlorosulfonyl Isocyanate," *Tetrahedron*, vol. 56: 381-387 (2000).
Renau, T. E., et al., "Synthesis of Non-nucleoside Analogs of Toyocamycin, Sangivamycin, and Thiosangivamycin: The Effect of Certain 4- and 4,6-Substituents on the Antiviral Activity of Pyrrolo[2,3-d]pyrimidines," *Journal of Medicinal Chemistry*, vol. 39: 3470-3476 (1996).
Secrist, J. A., et al., "(±)-3-(4-Amino-1H-pyrrolo[2,3-d]pyrimidin-1-yl)-5-(hydroxymethyl)-(1α,2α,3β,5β)-1,2-cyclopentanediol, the Carbocyclic Analogue of Tubercidin," *J. Med. Chem.*, vol. 27: 534-536 (1984).
Seela, F., et al., "Die isomeren 4-Amino-N-methylpyrrolo[2,3-d]pyrimidine," *Chemische Berichte*, vol. 114(6): 2056-2063 (1981).
Siddiqi, S. M., et al., "Search for New Purine- and Ribose-Modified Adenosine Analogues as Selective Agonists and Antagonists at Adenosine Receptors," *J. Med. Chem.*, vol. 38: 1174-1188 (1995).
Smith, M. E. B., et al., "An efficient route to all eight stereoisomers of a tri-functionalised cyclopentane scaffold for drug discovery," *Tetrahedron: Asymmetry*, vol. 12(5): 703-705 (2001).
Smith, M. E. B., et al., "Highly selective directed hydrogenation of enantiopure 4-(tert-butoxycarbonylamino)cyclopent-1-enecarboxylic acid methyl esters," *Tetrahedron Letters*, vol. 42: 1347-1350 (2001).
STN search, answer 255 of 273, (Jaeger et al. (Chemische Berichte, 1987), downloaded Mar. 6, 2017, pp. 1-3.
Sullivan, B., et al.,"Chemoensymatic formal synthesis of (−)-balanol. Provision of optical data for an often-reported intermediate," *Tetrahedron Letters*, vol. 49(35): 5211-5213 (2008).
Sun, L., et al., "Rational Design of 4,5-Disubstituted-5,7-dihydro-pyrrolo [2,3-d]pyrimidin-6-ones as a Novel Class of Inhibitors of Epidermal Growth Factor Receptor (EGF-R) and Her2(p185$^{erbB}$) Tyrosine Kiniases," *Bioorganic & Medicinal Chemistry Letters*, vol. 12: 2153-2157 (2002).
Talekar, R. R., et al., "Synthesis of some Pyrrol[2,3-d]pyrimidine and 1,2,3- Triazole Isonucleosides," *Tetrahedron*, vol. 53(10): 3831-3842 (1997).
Taylor, S. J. C., et al., "Development of the Biocatalytic Resolution of 2-azabicyclo[2.2.1]hept-5-en-3-one as an entry to Single-Enantiomer Carbocyclic Nucleosides," *Tetrahedron: Asymmetry*, vol. 4(6): 1117-1128 (1993).
Tumkevicius, S., et al., "Synthesis of Novel Thieno- and Pyrrolo [2,3-d] pyrimidines peri-Fused with Pyrimidine, 1,4-Diazepine and 1,4-Thiazepine Rings", *Synthesis*, No. 9:1377-1382 (2003).
Winum, J., et al., "N-(tert-Butoxycarbonyl)-N[4-(dimethylazaniumylidene)-1,4-dihydropyridin-1-yisulfonyl]azanide: A New Sulfamoylating Agent Structure and Reactivity toward Amines," *Organic Letters*, vol. 3(14): 2241-2243 (2001).
Winum, J., et al., "Carbonic Anhydrase Inhibitors, Inhibition of Cytosolic Isozymes I and II and Transmembrane, Tumor-Associated Isozyme IX with Sulfamates Including EMATE Also Acting as Steroid Sulfatase Inhibitors," *Journal of Medicinal Chemistry*, vol. 46(11):2197-2204 (2003).
Wood, M. R., et al., "A novel, one-step method for the conversion of primary alcohols into carbamate-protected amines," *Tetrahedron Letters*, 2002, vol. 43, pp. 3887-3890 (2002).

PROCESS FOR THE SYNTHESIS OF E1 ACTIVATING ENZYME INHIBITORS

PRIORITY CLAIM

This application claims priority from U.S. Provisional Patent Application Ser. No. 60/963,008, filed Aug. 2, 2007, and U.S. Provisional Patent Application Ser. No. 61/062,378, filed Jan. 25, 2008, both which are hereby incorporated by reference in their entirety.

FIELD OF THE INVENTION

The present invention relates to processes for the synthesis of E1 activating enzyme inhibitors and intermediates useful in such processes.

BACKGROUND OF THE INVENTION

The post-translational modification of proteins by ubiquitin-like molecules (ubls) is an important regulatory process within cells, playing key roles in controlling many biological processes including cell division, cell signaling and the immune response. Ubls are small proteins that are covalently attached to a lysine on a target protein via an isopeptide linkage with a C-terminal glycine of the ubl. The ubiquitin-like molecule alters the molecular surface of the target protein and can affect such properties as protein-protein interactions, enzymatic activity, stability and cellular localization of the target.

Ubiquitin and other ubls are activated by a specific E1 enzyme which catalyzes the formation of an acyl-adenylate intermediate with the C-terminal glycine of the ubl. The activated ubl molecule is then transferred to the catalytic cysteine residue within the E1 enzyme through formation of a thioester bond intermediate. The E1-ubl intermediate and an E2 associate, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein.

Targeting E1 activating enzymes provides a unique opportunity to interfere with a variety of biochemical pathways important for maintaining the integrity of cell division and cell signaling. E1 activating enzymes function at the first step of ubl conjugation pathways; thus, inhibition of an E1 activating enzyme will specifically modulate the downstream biological consequences of the ubl modification. As such, inhibition of these activating enzymes, and the resultant inhibition of downstream effects of ubl-conjugation, represents a method of interfering with the integrity of cell division, cell signaling, and several aspects of cellular physiology which are important for disease mechanisms. Thus, E1 enzymes such as UAE, NAE, and SAE, as regulators of diverse cellular functions, are potentially important therapeutic targets for the identification of novel approaches to treatment of diseases and disorders.

Langston S. et al. U.S. patent application Ser. No. 11/700,614, which is hereby incorporated by reference in its entirety, discloses compounds which are effective inhibitors of E1 activating enzymes, particularly NAE. The compounds are useful for inhibiting E1 activity in vitro and in vivo and are useful for the treatment of disorders of cell proliferation, particularly cancer, and other disorders associated with E1 activity. One class of compounds described in Langston et al. are 4-substituted ((1S, 2S, 4R)-2-hydroxy-4-{7H-pyrrolo[2,3-d]pyrimidin-7-yl}cyclopentyl)methyl sulfamates. Efficient chemical synthesis of these compounds can be challenging due to the multiple stereogenic centers in these compounds. There is, thus, a need for additional processes for the preparation of 4-substituted ((1S, 2S, 4R)-2-hydroxy-4-{7H-pyrrolo[2,3-d]pyrimidin-7-yl}cyclopentyl)methyl sulfamates.

DESCRIPTION OF THE INVENTION

The present invention provides processes and intermediates for the synthesis of 4-substituted ((1S, 2S, 4R)-2-hydroxy-4-{7H-pyrrolo[2,3-d]pyrimidin-7-yl}cyclopentyl) methyl sulfamates, which are useful as E1 activating enzyme inhibitors.

In one aspect the invention relates to a process for the synthesis of a compound of formula (I):

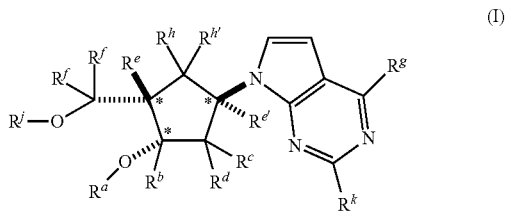

or a salt thereof; wherein:
stereochemical configurations depicted at asterisk positions indicate relative stereochemistry;
$R^a$ is hydrogen or a hydroxyl protecting group; or $R^a$ taken together with $R^j$ and the intervening atoms forms a cyclic diol protecting group; or $R^a$ taken together with $R^m$ and the intervening atoms forms a cyclic diol protecting group;
$R^b$ is hydrogen, fluoro, $C_{1-4}$ aliphatic or $C_{1-4}$ fluoroaliphatic;
$R^c$ is hydrogen, fluoro, chloro, —OH, —O—$R^m$ or optionally substituted $C_{1-4}$ aliphatic;
$R^d$ is hydrogen, fluoro, $C_{1-4}$ aliphatic or $C_{1-4}$ fluoroaliphatic;
$R^e$ is hydrogen or $C_{1-4}$ aliphatic;
$R^{e'}$ is hydrogen or $C_{1-4}$ aliphatic;
each $R^f$ is independently hydrogen, fluoro, $C_{1-4}$ aliphatic or $C_{1-4}$ fluoroaliphatic;
$R^g$ is chloro, fluoro, iodo or bromo;
$R^h$ is hydrogen, fluoro, $C_{1-4}$ aliphatic or $C_{1-4}$ fluoroaliphatic;
$R^{h'}$ is hydrogen, fluoro, $C_{1-4}$ aliphatic or $C_{1-4}$ fluoroaliphatic;
$R^j$ is hydrogen or a hydroxyl protecting group; or $R^j$ taken together with $R^a$ and the intervening atoms forms a cyclic diol protecting group;
$R^k$ is hydrogen or $C_{1-4}$ aliphatic;
$R^m$ is a hydroxyl protecting group; or $R^m$ taken together with $R^a$ and the intervening atoms forms a cyclic diol protecting group;

said process comprising the step of combining a compound of formula (II), or a salt thereof, with a compound of formula (III) to afford a compound of formula (I);

(II)

(III)

wherein:

stereochemical configurations depicted at asterisk positions indicate relative stereochemistry;

each of variables $R^a$, $R^b$, $R^c$, $R^d$, $R^e$, $R^{e'}$, $R^f$, $R^g$, $R^h$, $R^{h'}$, $R^j$, $R^k$, and $R^m$ in formulas (II) and (III) is as defined in formula (I);

$R^l$ is —CH$_2$CHO or —CH$_2$CH(OR$^{l'}$)$_2$; and each $R^{l'}$ is independently C$_{1-6}$ aliphatic, or two $R^{l'}$ are taken together with the intervening oxygen and carbon atoms to form an optionally substituted 5- or 6-membered cyclic acetal moiety.

In some embodiments, the process further comprises the step:

c) treating the compound of formula (I) with an amine of formula HNR$^n$R$^o$ to form a compound of formula (V), or a salt thereof;

(V)

wherein:

stereochemical configurations depicted at asterisk positions indicate relative stereochemistry;

each of variables $R^a$, $R^b$, $R^c$, $R^d$, $R^e$, $R^{e'}$, $R^f$, $R^h$, $R^{h'}$, $R^j$, $R^k$, and $R^m$ in formula (V) is as defined in formula (I);

$R^n$ is H or C$_{1-4}$ aliphatic; and $R^o$ is optionally substituted C$_{1-10}$ aliphatic, aryl, heteroaryl or heterocyclic.

In some embodiments, the process further comprises the step:

d) sulfamoylating a compound of formula (V), wherein $R^j$ is hydrogen to form a compound of formula (VI), or a salt thereof;

(VI)

wherein:

stereochemical configurations depicted at asterisk positions indicate relative stereochemistry;

each of variables $R^a$, $R^b$, $R^c$, $R^d$, $R^e$, $R^{e'}$, $R^f$, $R^h$, $R^{h'}$, $R^k$, $R^m$, $R^n$, and $R^o$ in formula (VI) is as defined in formula (V).

Another aspect of the invention relates to another process for forming a compound of formula (I):

(I)

or a salt thereof; wherein:

stereochemical configurations depicted at asterisk positions indicate relative stereochemistry;

$R^a$ is hydrogen or a protecting group; or $R^a$ taken together with $R^j$ and the intervening atoms forms a cyclic diol protecting group; or $R^a$ taken together with $R^m$ and the intervening atoms forms a cyclic diol protecting group;

$R^b$ is hydrogen, fluoro, C$_{1-4}$ aliphatic or C$_{1-4}$ fluoroaliphatic;

$R^c$ is hydrogen, fluoro, chloro, —OH, —O—R$^m$ or optionally substituted C$_{1-4}$ aliphatic;

$R^d$ is hydrogen, fluoro, C$_{1-4}$ aliphatic or C$_{1-4}$ fluoroaliphatic;

$R^e$ is hydrogen or C$_{1-4}$ aliphatic;

$R^{e'}$ is hydrogen or C$_{1-4}$ aliphatic;

each $R^f$ is independently hydrogen, fluoro, C$_{1-4}$ aliphatic or C$_{1-4}$ fluoroaliphatic;

$R^g$ is chloro, fluoro, iodo or bromo;

$R^h$ is hydrogen, fluoro, C$_{1-4}$ aliphatic or C$_{1-4}$ fluoroaliphatic;

$R^{h'}$ is hydrogen, fluoro, C$_{1-4}$ aliphatic or C$_{1-4}$ fluoroaliphatic;

$R^j$ is hydrogen or a protecting group; or $R^j$ taken together with $R^a$ and the intervening atoms forms a cyclic diol protecting group;

$R^k$ is hydrogen or C$_{1-4}$ aliphatic;

$R^m$ is a hydroxyl protecting group; or $R^m$ taken together with $R^a$ and the intervening atoms forms a cyclic diol protecting group;

said process comprising treating a compound of formula (IV):

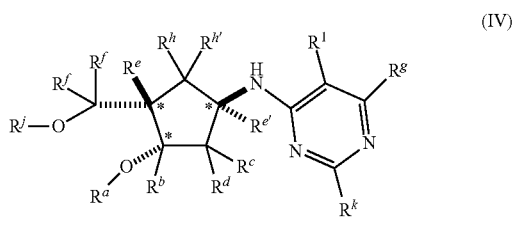

(IV)

with an acid to form the compound of formula (I), wherein:
each of variables $R^a$, $R^b$, $R^c$, $R^d$, $R^e$, $R^{e'}$, $R^f$, $R^h$, $R^{h'}$, $R^j$, $R^k$, and $R^m$ in formula (IV) is as defined in formula (I);
$R^i$ is —CH$_2$CH(OR$^{i'}$)$_2$; and
each $R^{i'}$ is independently C$_{1-6}$ aliphatic, or two $R^{i'}$ are taken together with the intervening oxygen and carbon atoms to form an optionally substituted 5- or 6-membered cyclic acetal moiety.

Another aspect of the invention relates to a process for forming a compound of formula (V):

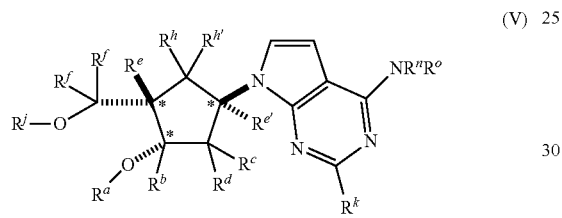

(V)

or a salt thereof; wherein:
stereochemical configurations depicted at asterisk positions indicate relative stereochemistry;
$R^a$ is hydrogen or a protecting group; or $R^a$ taken together with $R^j$ and the intervening atoms forms a cyclic diol protecting group; or $R^a$ taken together with $R^m$ and the intervening atoms forms a cyclic diol protecting group;
$R^b$ is hydrogen, fluoro, C$_{1-4}$ aliphatic or C$_{1-4}$ fluoroaliphatic;
$R^c$ is hydrogen, fluoro, chloro, —OH, —O—R$^m$ or optionally substituted C$_{1-4}$ aliphatic;
$R^d$ is hydrogen, fluoro, C$_{1-4}$ aliphatic or C$_{1-4}$ fluoroaliphatic;
$R^e$ is hydrogen or C$_{1-4}$ aliphatic;
$R^{e'}$ is hydrogen or C$_{1-4}$ aliphatic;
each $R^f$ is independently hydrogen, fluoro, C$_{1-4}$ aliphatic or C$_{1-4}$ fluoroaliphatic;
$R^h$ is hydrogen, fluoro, C$_{1-4}$ aliphatic or C$_{1-4}$ fluoroaliphatic;
$R^{h'}$ is hydrogen, fluoro, C$_{1-4}$ aliphatic or C$_{1-4}$ fluoroaliphatic;
$R^j$ is hydrogen or a hydroxyl protecting group; or $R^j$ taken together with $R^a$ and the intervening atoms forms a cyclic diol protecting group;
$R^k$ is hydrogen or C$_{1-4}$ aliphatic;
$R^m$ is a hydroxyl protecting group; or $R^m$ taken together with $R^a$ and the intervening atoms forms a cyclic diol protecting group.
$R^n$ is H or C$_{1-4}$ aliphatic;
$R^o$ is optionally substituted C$_{1-10}$ aliphatic, aryl, heteroaryl or heterocyclic;
said process comprising treating a compound of formula (Ia):

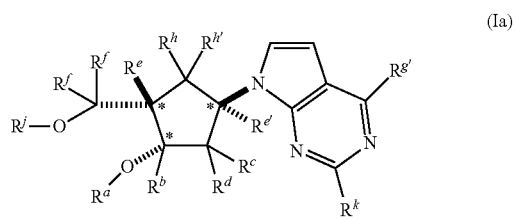

(Ia)

with an amine of formula HNR$^n$R$^o$, wherein:
each of variables $R^a$, $R^b$, $R^c$, $R^d$, $R^e$, $R^{e'}$, $R^f$, $R^h$, $R^{h'}$, $R^j$, $R^k$, and $R^m$ in formula (Ia) is as defined in formula (V); and
$R^{g'}$ is a leaving group.

Another aspect of the invention relates to compounds of formula (Ia):

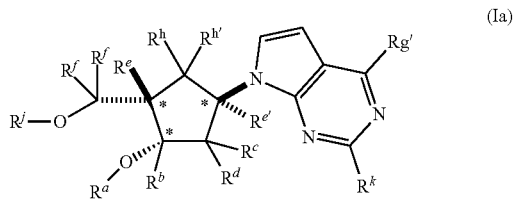

(Ia)

or a salt thereof; wherein:
stereochemical configurations depicted at asterisk positions indicate absolute stereochemistry;
$R^a$ is hydrogen or a protecting group; or $R^a$ taken together with $R^j$ and the intervening atoms forms a cyclic diol protecting group; or $R^a$ taken together with $R^m$ and the intervening atoms forms a cyclic diol protecting group;
$R^b$ is hydrogen, fluoro, C$_{1-4}$ aliphatic or C$_{1-4}$ fluoroaliphatic;
$R^c$ is hydrogen, fluoro, chloro, —OH, —O—R$^m$ or optionally substituted C$_{1-4}$ aliphatic;
$R^d$ is hydrogen, fluoro, C$_{1-4}$ aliphatic or C$_{1-4}$ fluoroaliphatic;
$R^e$ is hydrogen or C$_{1-4}$ aliphatic;
$R^{e'}$ is hydrogen or C$_{1-4}$ aliphatic;
each $R^f$ is independently hydrogen, fluoro, C$_{1-4}$ aliphatic or C$_{1-4}$ fluoroaliphatic;
$R^{g'}$ is a leaving group;
$R^h$ is hydrogen, fluoro, C$_{1-4}$ aliphatic or C$_{1-4}$ fluoroaliphatic;
$R^{h'}$ is hydrogen, fluoro, C$_{1-4}$ aliphatic or C$_{1-4}$ fluoroaliphatic;
$R^j$ is hydrogen or a hydroxyl protecting group; or $R^j$ taken together with $R^a$ and the intervening atoms forms a cyclic diol protecting group;
$R^k$ is hydrogen or C$_{1-4}$ aliphatic; and
$R^m$ is a hydroxyl protecting group; or $R^m$ taken together with $R^a$ and the intervening atoms forms a cyclic diol protecting group.

Another aspect of this invention relates to compounds of formula (IIa):

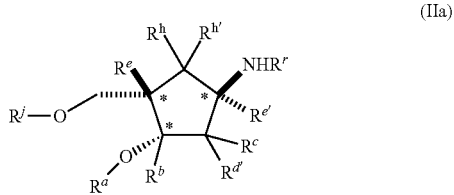

(IIa)

or a salt thereof; wherein:

stereochemical configurations depicted at asterisk positions indicate absolute stereochemistry;

$R^a$ is hydrogen or a protecting group; or $R^a$ taken together with $R^j$ and the intervening atoms forms a cyclic diol protecting group; or $R^a$ taken together with $R^m$ and the intervening atoms forms a cyclic diol protecting group;

$R^b$ is hydrogen, fluoro, $C_{1-4}$ aliphatic or $C_{1-4}$ fluoroaliphatic;

$R^c$ is hydrogen, fluoro, chloro, —OH, —O—$R^m$ or optionally substituted $C_{1-4}$ aliphatic;

$R^{d'}$ is hydrogen, fluoro, bromo, $C_{1-4}$ aliphatic or $C_{1-4}$ fluoroaliphatic;

$R^e$ is hydrogen or $C_{1-4}$ aliphatic;

$R^{e'}$ is hydrogen or $C_{1-4}$ aliphatic;

$R^h$ is hydrogen, fluoro, $C_{1-4}$ aliphatic or $C_{1-4}$ fluoroaliphatic;

$R^{h'}$ is hydrogen, fluoro, $C_{1-4}$ aliphatic or $C_{1-4}$ fluoroaliphatic;

$R^j$ is hydrogen or a hydroxyl protecting group; or $R^j$ taken together with $R^a$ and the intervening atoms forms a cyclic diol protecting group;

$R^m$ is a hydroxyl protecting group; or $R^m$ taken together with $R^a$ and the intervening carbon atoms forms a cyclic diol protecting group; and $R^r$ is hydrogen or an amine protecting group.

Compounds and processes of this invention include those described generally above, and are further illustrated by the detailed descriptions of processes and compounds given below. Terms used herein shall be accorded the following defined meanings, unless otherwise indicated.

As used herein, the term "E1," "E1 enzyme," or "E1 activating enzyme" refers to any one of a family of related ATP-dependent activating enzymes involved in activating or promoting ubiquitin or ubiquitin-like (collectively "ubl") conjugation to target molecules. E1 activating enzymes function through an adenylation/thioester intermediate formation to transfer the appropriate ubl to the respective E2 conjugating enzyme through a transthiolation reaction. The resulting activated ubl-E2 promotes ultimate conjugation of the ubl to a target protein. A variety of cellular proteins that play a role in cell signaling, cell cycle, and protein turnover are substrates for ubl conjugation which is regulated through E1 activating enzymes (e.g., NAE, UAE, SAE). Unless otherwise indicated by context, the term "E1 enzyme" is meant to refer to any E1 activating enzyme protein, including, without limitation, nedd8 activating enzyme (NAE (APPBP1/Uba3)), ubiquitin activating enzyme (UAE (Uba1)), sumo activating enzyme (SAE (Aos1/Uba2)), or ISG15 activating enzyme (Ube1L), preferably human NAE, SAE or UAE, and more preferably NAE.

The term "E1 enzyme inhibitor" or "inhibitor of E1 enzyme" is used to signify a compound having a structure as defined herein, which is capable of interacting with an E1 enzyme and inhibiting its enzymatic activity. Inhibiting E1 enzymatic activity means reducing the ability of an E1 enzyme to activate ubiquitin like (ubl) conjugation to a substrate peptide or protein (e.g., ubiquitination, neddylation, sumoylation).

The term "aliphatic" or "aliphatic group", as used herein, means a substituted or unsubstituted straight-chain, branched or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, alkynyl groups and hybrids thereof, such as (cycloalkyl)alkyl, (cycloalkenyl) alkyl or (cycloalkyl)alkenyl. In various embodiments, the aliphatic group has 1 to 12, 1 to 8, 1 to 6, 1 to 4, or 1 to 3 carbons.

The terms "alkyl", "alkenyl", and "alkynyl", used alone or as part of a larger moiety, refer to a straight and branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring. The term "cycloaliphatic" may be used interchangeably with the terms "carbocycle", "carbocyclyl", "carbocyclo", or "carbocyclic".

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$)alkyl, or $C_{6-10}$ aryl($C_{1-3}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclic", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl) or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro. Nonlimiting examples of fluoroaliphatics include —$CH_2F$, —$CHF_2$, —$CF_3$, —$CH_2CF_3$, —$CF_2CH_3$, and —$CF_2CF_3$.

The term "linker group" or "linker" means an organic moiety that connects two parts of a compound. Linkers typically comprise an atom such as oxygen or sulfur, a unit such as —NH—, —$CH_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-6}$ alkylene chain.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R*)—, —C≡C—, —O—, —S—, —S(O)—, —S(O)$_2$—, —S(O)$_2$N(R$^+$)—, —N(R*)—, —N(R$^+$)CO—, —N(R$^+$)C(O)N(R$^+$)—, —N(R$^+$)CO$_2$—, —C(O)N(R$^+$)—, —C(O)—, —C(O)—C(O)—, —CO$_2$—, —OC(O)—, —OC(O)O—, —OC(O)N(R$^+$)—, —C(NR$^+$)=N—, —C(OR*)=N—, —N(R$^+$)—N(R$^+$)—, or —N(R$^+$)S(O)$_2$—. Each R$^+$, independently, is hydrogen or an optionally substituted aliphatic, aryl, heteroaryl, or heterocyclyl group, or two R$^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each R* independently is hydrogen or an optionally substituted aliphatic, aryl, heteroaryl, or heterocyclyl group.

Examples of $C_{3-6}$ alkylene chains that have been "interrupted" with —O— include —CH$_2$OCH$_2$—, —CH$_2$O(CH$_2$)$_2$—, —CH$_2$O(CH$_2$)$_3$—, —CH$_2$O(CH$_2$)$_4$—, —(CH$_2$)$_2$OCH$_2$—, —(CH$_2$)$_2$O(CH$_2$)$_2$—, —(CH$_2$)$_2$O(CH$_2$)$_3$—, —(CH$_2$)$_3$O(CH$_2$)—, —(CH$_2$)$_3$O(CH$_2$)$_2$—, and —(CH$_2$)$_4$O(CH$_2$)—. Other examples of alkylene chains that are "interrupted" with functional groups include —CH$_2$ZCH$_2$—, —CH$_2$Z(CH$_2$)$_2$—, —CH$_2$Z(CH$_2$)$_3$—, —CH$_2$Z(CH$_2$)$_4$—, —(CH$_2$)$_2$ZCH$_2$—, —(CH$_2$)$_2$Z(CH$_2$)$_2$—, —(CH$_2$)$_2$Z(CH$_2$)$_3$—, —(CH$_2$)$_3$Z(CH$_2$)—, —(CH$_2$)$_3$Z(CH$_2$)$_2$—, and —(CH$_2$)$_4$Z(CH$_2$)—, wherein Z is one of the "interrupting" functional groups listed above.

One of ordinary skill in the art will recognize that when an alkylene chain having an interruption is attached to a functional group, certain combinations are not sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

As used herein, the term "independently selected" means that the same or different values may be selected for multiple instances of a given variable in a single compound.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —NO$_2$, —CN, —R*, —C(R*)=C(R*)$_2$, —C≡C—R*, —OR*, —SR$^{oo}$, —S(O)R$^{oo}$, —SO$_2$R$^{oo}$, —SO$_3$R$^{oo}$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^{oo}$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(O)N(R$^+$)C(=NR$^+$)—N(R$^+$)$_2$, —N(R$^+$)C(=NR$^+$)—N(R$^+$)—C(O)R*, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^{oo}$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, wherein R$^{oo}$ is an optionally substituted aliphatic or aryl group, and R$^+$ and R* are as defined above, or two adjacent substituents, taken together with their intervening atoms, form a 5-6 membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following; =O, =S, =C(R*)$_2$, =N—N(R*)$_2$, =N—OR*, =N—NHC(O)R*, =N—NHCO$_2$R$^{oo}$, =N—NHSO$_2$R$^{oo}$, or =N—R*, where each R* and R$^{oo}$ is as defined above.

Suitable substituents on the nitrogen atom of a non-aromatic heterocyclic ring include —R*, —N(R*)$_2$, —C(O)R*, —CO$_2$R*, —C(O)—C(O)R*—C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*; wherein each R* is as defined above.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to".

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

It also will be apparent to one skilled in the art that certain compounds of this invention may exist in tautomeric forms, all such tautomeric forms of the compounds being within the scope of the invention. Unless stereochemical configuration is expressly defined, structures depicted herein are meant to include all stereochemical forms of the structure; i.e., the R and S configurations for each asymmetric center. Therefore, unless otherwise indicated, single stereochemical isomers as well as enantiomeric and diastereomeric mixtures of the present compounds are within the scope of the invention. By way of example, the compounds of formula (VI) wherein R$^c$ is —OH can have R or S configuration at the carbon atom bearing $R^c$. Both the R and the S stereochemical isomers, as well as all mixtures thereof, are included within the scope of the invention.

Where stereochemical configuration at a given asymmetric center is defined by structure, unless stated otherwise, the depicted configuration indicates stereochemistry relative to other asymmetric centers in the molecule. Where stereochemical configuration is defined by chemical name, the designations (rel), (R*), and (S*) indicate relative stereochemistry, while the designations (R), (S), (+), (−), and (abs) indicate absolute stereochemistry.

In the compounds of formula (I)-(VI), stereochemical configurations depicted at asterisked positions indicate relative stereochemistry, unless expressly stated to indicate absolute stereochemistry. Preferably, the diastereomeric purity of the compound is at least 80%, more preferably at least 90%, still more preferably at least 95%, and most preferably at least 99%. As used herein, the term "diastereomeric purity" refers to the amount of a compound having the depicted relative stereochemistry, expressed as a percentage of the total amount of all diastereomers present.

In some embodiments, stereochemical configurations depicted at asterisked positions indicate absolute as well as relative stereochemistry. Preferably, the enantiomeric purity of the compound is at least 80%, more preferably at least 90%, still more preferably at least 95%, and most preferably at least 99%. As used herein, the term "enantiomeric purity" refers to the amount of a compound having the depicted absolute stereochemistry, expressed as a percentage of the total amount of the depicted compound and its enantiomer.

Methods for determining diastereomeric and enantiomeric purity are well-known in the art. Diastereomeric purity can be determined by any analytical method capable of quantitatively distinguishing between a compound and its diastereomers. Examples of suitable analytical methods include, without limitation, nuclear magnetic resonance spectroscopy (NMR), gas chromatography (GC), and high performance liquid chromatography (HPLC). Similarly, enantiomeric purity can be determined by any analytical method capable of quantitatively distinguishing between a compound and its enantiomer. Examples of suitable analytical methods include, without limitation, GC or HPLC using a chiral column packing material. Enantiomers may also be distinguishable by GC or HPLC using an achiral column packing material if first derivatized with an optically enriched derivatizing agent, e.g., Mosher's acid. Similarly, enantiomers may also be distinguishable by NMR if first derivatized with an optically enriched derivatizing agent.

As used herein, the term "hydroxyl protecting group" refers to a chemical group that: i) reacts with a hydroxyl functional group of a substrate to form a protected substrate; ii) is stable to reaction conditions to which the protected substrate will be subjected; and iii) is removable from a protected substrate to liberate the hydroxyl functional group under conditions that are compatible with other functionality present in the substrate. As used herein, the term "cyclic diol protecting group" refers to a chemical group that: i) reacts with a diol functional group of a substrate to form a protected substrate; ii) is stable to reaction conditions to which the protected substrate will be subjected; and iii) is removable from a protected substrate to liberate the diol functional group under conditions that are compatible with other functionality present in the substrate. The hydroxyl groups of 1,2- and 1,3-diols may be individually protected with hydroxyl protecting groups or may be jointly protected with a cyclic diol protecting group.

As used herein the term "acid labile protecting group" refers to a chemical group that: i) reacts with a functional group of substrate to form a protected substrate; ii) is stable to reaction conditions to which the protected substrate will be subjected, and iii) is removable from a protected substrate to liberate the functional group under acidic conditions that are compatible with other functionality present in the substrate. Amine and hydroxyl groups are among the functional groups that may be protected with an acid-labile protecting group.

As used herein the term "amine protecting group" refers to a chemical group that: i) reacts with an amine functional group of a substrate to form a protected substrate; ii) is stable to reaction conditions to which the protected substrate will be subjected; and iii) is removable from a protected substrate to liberate the amine under conditions that are compatible with other functionality present in the substrate.

Hydroxyl protecting groups, cyclic diol protecting groups, acid-labile protecting groups and amine protecting groups that are suitable for use in the processes and compounds of the present invention are known to those of ordinary skill in the art. The chemical properties of such protecting groups, methods for their introduction and their removal can be found, for example, in P. G. M. Wuts and T. W. Greene, *Greene's Protective Groups in Organic Synthesis* (4$^{th}$ed.), John Wiley & Sons, NJ (2007).

The processes and compounds of the present invention are further illustrated by the detailed descriptions and illustrative examples given below.

In a first aspect, the invention relates to a process for forming a compound of formula (I) by combining a compound of formula (II) with a compound of formula (III). In one embodiment, wherein $R^i$ is —CH$_2$CH(OR$^{i'}$)$_2$, and each $R^{i'}$ is independently C$_{1-6}$ aliphatic, or two $R^{i'}$ are taken together with the intervening oxygen and carbon atoms to form an optionally substituted 5- or 6-membered cyclic acetal moiety, the process comprises the steps:

a) treating a compound of formula (II), or a salt thereof, with a compound of formula (III) in the presence of a base to afford a compound of formula (IV); and b) treating a reaction mixture comprising the compound of formula (IV) with an acid to form the compound of formula (I).

Step a) involves a nucleophilic displacement reaction between a compound of formula (II) and a compound of formula (III) to form compounds of formula (IV). Compounds of formula (IV) may be then converted to compounds of formula (I) without isolation by the conditions of step b). Alternatively, compounds of formula (IV) can be isolated and/or purified by methods known to those of ordinary skill in the art and converted to compounds of formula (I) in a separate reaction. (See J. A. Secrist et al. *J. Med. Chem.*, 1984, 27, 534-536; R. B. Talekar and R. H. Wightman *Tetrahedron*, 1997, 53, 3831-3842). Step b) involves treatment with an acid, leading to the acid-catalyzed removal of the acetal groups along with cyclization to form the 7H-pyrrolo[2,3-d]pyrimidin-7-yl ring system.

Step a) may be conveniently carried out in the presence of a base such as an alkaline earth metal base or an organic amine base. Examples of an alkaline earth metal base include, but are not limited to, potassium carbonate, sodium carbonate, calcium carbonate, lithium hydroxide, potassium hydroxide, sodium hydroxide, lithium hydrogen carbonate, potassium hydrogen carbonate, sodium hydrogen carbonate, lithium hydride, potassium hydride, sodium hydride, lithium tert-butoxide, potassium tert-butoxide, and sodium tert-butoxide. Other alkaline earth metal bases include, but are not limited to, cesium carbonate, and cesium hydroxide. Organic amine bases include, but are not limited to, trialkylamines, cyclic amines, pyridines and substituted pyridines. Examples of these include, but are not limited to, triethylamine, triethylenediamine, pyridine, collidine, 2,6-lutidine, 4-dimethylaminopyridine, di-tertbutylpyridine, N-methylmorpholine, N-methylpiperidine, tetramethylguanidine, diazabicyclo[5.4.0]undec-7-ene (DBU), 1,4-diazabicyclo[2.2.2]octane, 1,5-diazabicycle[4.3.0]non-5-ene and N,N'-diisopropylethylamine. Other organic amine bases include, but are not limited to, 1-azabicyclo[2.2.2]octane, tributylamine and tripropylamine. Preferably, the base used in step a) is selected from potassium carbonate, potassium hydrogen carbonate, sodium carbonate, sodium hydrogen carbonate, sodium hydroxide, potassium hydroxide, triethylamine, N,N'-diisopropylethylamine, pyridine, and 2,6-lutidine.

The treating of step a) may be performed at ambient or elevated reaction temperature, though elevated temperatures may result in shorter reaction times. The selection of an appropriate reaction temperature and reaction time will depend largely on the base and solvent used. One of ordinary skill in the art will be able to select a suitable reaction temperature and reaction time in view of the reaction conditions being used.

In some embodiments, step a) may be carried out at reaction temperatures of at least about 20° C., 45° C. or 60° C. In some embodiments, step a) may be carried out at reaction temperatures no greater than 120° C., 105° C. or 90° C. Any ranges encompassing these high and low temperatures are included within the scope of the invention. Step a) is preferably performed at reaction temperatures in the range of about 20° C. to about 120° C., about 45° C. to about 105° C., or about 60° C. to about 90° C.

The acid used in step b) is a mineral acid or an organic acid. Examples of mineral acids include, but are not limited to, hydrochloric acid, sulfuric acid, hydrobromic acid, nitric acid and phosphoric acid. Examples of organic acids include but are not limited to acetic acid, propionic acid, benzoic acid, formic acid, oxalic acid, trichloroacetic acid, trifluoroacetic acid, methanesulfonic acid, p-toluensulfonic acid and trifluoromethanesulfonic acid. Preferably, the acid in step b) is selected from the group consisting of hydrochloric acid, sulfuric acid, trifluoroacetic acid, p-toluenesulfonic acid, trichloroacetic acid, acetic acid, and formic acid.

The treating of step b) is preferably performed at ambient or elevated reaction temperature, though elevated temperatures may result in shorter reaction times. The selection of an appropriate reaction temperature and reaction time will depend largely on the acid and solvent used. One of ordinary skill in the art will be able to select a suitable reaction temperature and reaction time in view of the reaction conditions being used.

In some embodiments, step b) may be carried out at reaction temperatures of at least about 20° C., 40° C. or 50° C. In some embodiments, step b) may be carried out at reaction temperatures no greater than about 90° C., 70° C., 60° C. or 50° C. Any ranges encompassing these high and low temperatures are included within the scope of the invention. Step b) is preferably performed at reaction temperatures in the range of about 20° C. to about 90° C., about 40° C. to about 60° C., or about 50° C. to about 60° C. In some other embodiments, step b) is preferably performed at a reaction temperature in the range of about 45° C. to about 60° C.

In some embodiments, step a) and step b) independently are carried out in a solvent or diluent comprising one or more of ethanol, isopropanol, sec-butanol, ethyl acetate, methylene chloride, chloroform, carbon tetrachloride, tetrahydrofuran, 2-methyltetrahydrofuran, dimethoxyethane, 1,4-dioxane, toluene, anisole, acetonitrile, N,N'-dimethylformamide, N,N'-dimethylacetamide, N-methylpyrrolidinone, dimethylsulfoxide, or mixtures thereof. In certain embodiments, each of step a) and step b) is carried out in a solvent comprising aqueous ethanol, aqueous isopropanol, aqueous sec-butanol, aqueous tetrahydrofuran, aqueous 1,4-dioxane, or mixtures thereof. In some embodiments, each of step a) and step b) is carried out in a solvent comprising ethanol, isopropanol, sec-butanol, tetrahydrofuran or 1,4-dioxane, or a mixture thereof.

In some embodiments, after the reaction is complete, the reaction mixture is allowed to cool to ambient temperature, concentrated and then added to an aqueous solution, following which the resulting product is collected by filtration and dried. In some embodiments, the concentrated reaction mixture is added to water. In some other embodiments, the concentrated reaction mixture is added to aqueous sodium chloride solution. In yet some other embodiments, the concentrated reaction mixture is added to an aqueous basic solution to neutralize the acid introduced in step b). Examples of aqueous basic solution include, but are not limited to, aqueous sodium carbonate, aqueous potassium carbonate and aqueous sodium bicarbonate.

Preferably, the process comprising steps a) and b) to form compounds of formula (I), wherein $R^I$ is —$CH_2CH(OR^{I'})_2$ is characterized by at least one of the following features:
  (i) the base in step a) is triethylamine;
  (ii) the treating of step a) is carried out in aqueous isopropanol;
  (iii) the treating of step b) is carried out in aqueous isopropanol;
  (iv) the acid in step b) is hydrochloric acid;
  (v) the treating of step a) is performed at a reaction temperature in the range of about 60° C. to about 90° C.; and
  (vi) the treating of step b) is performed at a reaction temperature in the range of about 40° C. to about 60° C.

In some embodiments, wherein $R^I$ is —$CH_2CH(OR^{I'})_2$, the compounds of formula (IV) can be isolated and optionally purified by methods known to those of ordinary skill in the art and converted to compounds of formula (I) in a separate reaction. In such embodiments, the conditions are as described above for step b). Preferably, the process for forming the compound of formula (I) from the compound of formula (IV), wherein $R^I$ is —$CH_2CH(OR^{I'})_2$ is characterized by at least one of the following features:
  (i) the treating is carried out in aqueous isopropanol;
  (ii) the acid is hydrochloric acid; and
  (iii) the treating is performed at a reaction temperature in the range of about 50° C. to about 60° C.

In another embodiment, the process for forming a compound of formula (I) comprises treating a compound of formula (II) with a compound of formula (III), wherein $R^I$ is —$CH_2CHO$, in the presence of a base. In this embodiment, the combination of compounds of formula (II) and formula (II) to form a compound of formula (I) occurs in a single step, step aa):
  aa) treating a compound of formula (II), or a salt thereof, with a compound of formula (II) in the presence of a base.

Suitable and preferred bases, solvents and reaction temperatures for step aa) are as described above for step a).

Preferably, the process for forming a compound of formula (I) comprising treating a compound of formula (II)

with a compound of formula (II), wherein $R^1$ is —CH$_2$CHO, in the presence of a base is characterized by at least one of the following features:
(i) the base in step aa) is triethylamine;
(ii) the treating of step aa) is carried out in isopropanol; and
(iii) the treating of step aa) is performed at a reaction temperature in the range of about 60° C. to about 90° C.

In some embodiments, after the reaction is complete, the reaction mixture is allowed to cool to ambient temperature, concentrated and then added to an aqueous solution, following which the resulting product is collected by filtration and dried. In some embodiments, the concentrated reaction mixture is added to water. In some other embodiments, the concentrated reaction mixture is added to aqueous sodium chloride solution. In yet some other embodiments, the concentrated reaction mixture is added to an aqueous basic solution. Examples of aqueous basic solution include, but are not limited to, aqueous sodium carbonate, aqueous potassium carbonate and aqueous sodium bicarbonate.

In some embodiments, the process described above further comprises the step
c) treating the compound of formula (I) with an amine of formula HNR″R° to form a compound of formula (V), or a salt thereof.

In some embodiments, step c) may be conveniently carried out in the presence of an acid or a base. In some embodiments, the base is an alkaline earth metal base or an organic amine base. Examples of such bases are described above for step a). Preferably the base in step c) is selected from potassium carbonate, potassium hydrogen carbonate, sodium carbonate, sodium hydrogen carbonate, sodium hydroxide, potassium hydroxide, triethylamine, N,N'-diisopropylethylamine, pyridine and 2,6-lutidine. The base can be used in equimolar amounts, in excess, or, if appropriate, as the solvent for the reaction.

In some embodiments the treating of step c) is carried out in a solvent or diluent comprising one or more of ethanol, isopropanol, sec-butanol, n-butanol, ethyl acetate, methylene chloride, chloroform, carbon tetrachloride, tetrahydrofuran, 2-methyltetrahydrofuran, dimethoxyethane, 1,4-dioxane, toluene, anisole, N,N'-dimethylformamide, N,N'-dimethylacetamide, N-methylpyrrolidinone, dimethylsulfoxide, diglyme, or mixtures thereof. In some embodiments, step c) may be carried out in water, or an aqueous solvent mixture comprising one of more of the solvents listed above. In some embodiments, step c) may be carried out without a solvent or diluent by employing an excess of the amine HNR″R°. In some embodiments, the treating of step c) is carried out in a solvent or diluent compromising one or more of toluene, anisole, N,N'-dimethylformamide, sec-butanol, diglyme, dimethylacetamide or N-methylpyrrolidinone.

The treating of step c) is preferably performed at ambient or elevated reaction temperatures. In some embodiments, the treating of step c) is performed under microwave irradiation conditions. The selection of an appropriate reaction temperature and reaction time will depend largely on the base and solvent used. One skilled in the art will be able to select a suitable reaction temperature and reaction time in view of the reaction conditions being used.

In some embodiments, step c) may be carried out at reaction temperatures of at least about 50° C., 90° C. or 130° C. In some embodiments, step c) may be carried out at reaction temperatures no greater than about 160° C. or 145° C. Any ranges encompassing these high and low reaction temperatures are included within the scope of the invention. Step c) is preferably performed at reaction temperatures in the range of about 50° C. to about 160° C., about 90° C. to about 145° C., or about 130° C. to about 145° C.

The treating of step c) may optionally be conducted under an elevated reaction pressure. One skilled in the art will be able to select a suitable reaction pressure in view of the reaction conditions being used. In some embodiments, step c) may be carried out at reaction pressures of at least about 50 psi or 70 psi. In some embodiments, step c) may be carried out at reaction pressures no greater than about 120 psi or 110 psi. Any ranges encompassing these high and low reaction pressures are included within the scope of the invention. If an elevated reaction pressure is employed in step c), it is preferably performed at reaction pressures in the range of about 50 psi to about 120 psi, or about 70 psi to about 110 psi. In some other embodiments, if an elevated reaction pressure is employed in step c), it is preferably in the range of about 70 psi to about 100 psi.

In some embodiments, following the completion of step c), the reaction mixture is cooled to ambient temperature and pressure and extracted with a solvent such as ethyl acetate, isopropyl acetate, methyl ethyl ketone, methyl isobutyl ketone, toluene, or tert-butyl methyl ether. In some other embodiments, following the completion of step c), the reaction mixture is cooled to ambient temperature and pressure, concentrated and added directly to water or a solvent such as ethyl acetate, methylene chloride, acetone, isopropyl acetate, methyl ethyl ketone, methyl isobutyl ketone, toluene, tert-butyl methyl ether, diethyl ether or acetonitrile to effect product precipitation. The product is then collected by filtration and dried.

Preferably, the process for forming a compound of formula (V) from a compound of formula (I) comprising step c) is characterized by at least one of the following features:
(i) said base of step c) is N,N'-diisopropylethylamine;
(ii) the treating of step c) is carried out in sec-butanol;
(iii) the treating of step c) is performed at a reaction temperature in the range of about 130° C. to about 145° C.; and
(iv) the treating of step c) is performed at a reaction pressure in the range of about 70 psi to about 100 psi.

The invention also relates to a process for the formation of a compound of formula (V) as defined above, comprising the treatment of a compound of formula (Ia) as defined above with an amine of formula HNR″R°. In some embodiments $R^{g'}$ is halo, —O—$R^s$, —S—$R^t$, —S(O)$R^t$ or —S(O)$_2$$R^t$; wherein $R^s$ is C$_{1-4}$ aliphatic, alkylsulphonyl, fluoroalkylsulphonyl, optionally substituted aryl or optionally substituted arylsulphonyl and $R^t$ is optionally substituted C$_{1-4}$ aliphatic or optionally substituted aryl.

Compounds of formula (Ia) wherein $R^{g'}$ is —O—$R^s$, —S—$R^t$, —S(O)$R^t$ or —S(O)$_2$$R^t$ may be prepared from compounds of formula (I) by methods known to those of skill in the art. For example, $R^g$ in a compound of formula (I) may be displaced with an alkoxide or a thiol to generate compounds of formula (Ia) where $R^{g'}$ is —O—$R^s$, —S—$R^t$, wherein $R^s$ is optionally substituted C$_{1-4}$ aliphatic or optionally substituted aryl or $R^t$ is optionally substituted C$_{1-4}$ aliphatic or optionally substituted aryl. Compounds wherein $R^{g'}$ is —S—$R^t$ may be further oxidized to generate compounds wherein $R^{g'}$ is —S(O)$R^t$ or —S(O)$_2$$R^t$.

To generate compounds of formula (Ia), wherein $R^{g'}$ is —O—$R^s$ when $R^s$ is alkylsulfonyl, fluoroalkylsulphonyl or optionally substituted arylsulphonyl, $R^g$ in the compound of formula (I) must first be converted to a hydroxyl group, followed by treatment with the appropriate sulfonylchloride or anhydride. Conversion of $R^g$ to the hydroxyl group may be accomplished directly by treatment under basic conditions such as NaOH, or alternatively from a compound of formula (Ia) wherein $R^{g'}$ is —OCH$_3$, which can be hydrolyzed to the corresponding alcohol by treatment with aqueous NaOH or trimethylsilylchloride/sodium iodide.

The displacement of $R^{g'}$ in compounds of formula (Ia) with HNR″R° may be conveniently carried out in the presence of a base such as an alkaline earth metal base or an organic amine base. Examples of suitable bases are described above for step c). The base can be used in an equimolar amount, in excess, or, if appropriate, as the solvent for the reaction.

The displacement of $R^{g'}$ in compounds of formula (Ia) with HNR″R° may be conveniently carried out in the presence of a suitable solvent or diluent. Examples of suitable solvents are described above for step c). In some embodiments the displacement of $R^{g'}$ may be carried out without a solvent or diluent by employing an excess of the amine HNR″R°.

The displacement of $R^{g'}$ in compounds of formula (Ia) with HNR″R° is preferably performed at ambient or elevated reaction temperatures. Suitable temperatures and ranges of temperatures are as described above for step c).

The displacement of $R^{g'}$ in compounds of formula (Ia) with HNR″R° may optionally be conducted under an elevated reaction pressure. Suitable pressures and ranges of pressures are as described above for step c).

In some embodiments the displacement of $R^{g'}$ in compounds of formula (Ia) with HNR″R° may also be carried out in the presence of a palladium catalyst/ligand system. Suitable metal catalyst systems are such as those described in Prim D. et al. *Tetrahedron,* 2002, 58, 20412 and Gunda P. et al. *Angew. Chem. Intl. Ed.,* 2004, 43, 6372. Suitable bases include but are not limited to sodium tert-butoxide, cesium carbonate and K$_3$PO$_4$. Suitable solvents include but are not limited to toluene, 1,4-dioxane, tert-butanol and mixtures thereof.

In some embodiments when a palladium-catalyst/ligand system is employed, $R^{g'}$ is chloride, bromide, iodide, triflate or —O—R$^s$ where R$^s$ is optionally substituted arylsulfonyl. In certain such embodiments $R^{g'}$ is chloride, bromide or triflate.

In some embodiments, the process of the invention further comprises the step:
d) sulfamoylating a compound of formula (V), wherein R$^j$ is hydrogen, to form a compound of formula (VI), or a salt thereof;

(VI)

wherein:
stereochemical configurations depicted at asterisk positions indicate relative stereochemistry; and
each of variables $R^a$, $R^b$, $R^c$, $R^d$, $R^e$, $R^{e'}$, $R^f$, $R^h$, $R^{h'}$, $R^k$, $R^m$, $R^n$, and R° in formula (VI) is as defined in formula (V).

Compounds of formula (VI), which are effective inhibitors of E1 activating enzymes, particularly NAE, are disclosed in Langston S. et al. U.S. patent application Ser. No. 11/700,614, which is hereby incorporated by reference in its entirety, including all formulas, and all genus and sub-genus descriptions disclosed therein.

If R$^j$ in a compound of formula (V) is other than hydrogen, i.e., if R$^j$ is a hydroxyl protecting group, it must be removed prior to the conversion to a compound of formula (VI). The deprotection step can be accomplished by methods known to one of ordinary skill in the art.

In some embodiments, the sulfamoylating step d) comprises the steps:
I-A) treating a base in a solvent with a solution of R″NHS(O)$_2$Cl wherein R″ is hydrogen or an acid-labile protecting group;
II-A) treating the reaction mixture formed in I-A) with the compound of formula (V); and
III-A) optionally treating the reaction mixture formed in II-A) with an acid.

Steps d) I-A), II-A) and III-A) may be conveniently carried out in the presence of a suitable solvent or diluent, which may be the same or different for each of steps d) I-A), II-A) and III-A). Examples of suitable solvents, include but are not limited to, ethyl acetate, methylene chloride, chloroform, carbon tetrachloride, tetrahydrofuran, 2-methyltetrahydrofuran, 1,4-dioxane, dimethoxyethane, toluene, anisole, acetonitrile, N,N'-dimethylformamide, N,N'-dimethylacetamide, N-methylpyrrolidinone, dimethylsulfoxide, and mixtures thereof. In some embodiments, steps d) I-A), II-A) and III-A) are each carried out in a solvent comprising ethyl acetate, tetrahydrofuran, 2-methyltetrahydrofuran, dimethoxyethane, acetonitrile, N,N'-dimethylacetamide, N-methylpyrrolidinone, DME, or mixtures thereof.

The base in step d) I-A) is an organic amine base. Examples of organic amine bases include, but are not limited to, trialkylamines, pyridine and substituted pyridines. Examples of these include but are not limited to trimethylamine, triethylamine, triethylenediamine, pyridine, collidine, 2,6-lutidine, 4-dimethylaminopyridine, 2,6-di-tert-butylpyridine, 2,6-di-tert-butyl-4-methylpyridine, 1-azabicyclo[2.2.2]octane, tributylamine, tripropylamine, diazabicyclo[5.4.0]undec-7-ene (DBU), 1,4-diazabicyclo[2.2.2]octane, 1,5-diazabicycle[4.3.0]non-5-ene, sparteine, and N,N'diisopropylethylamine.

In some embodiments in step d) I-A), R″NHS(O)$_2$Cl is added to the solvent at a rate sufficient to keep the temperature of the reaction below about 15° C.; and in step d) II-A), the reaction mixture is cooled, preferably to between about −10° C. and 0° C., and then the compound of formula (V) is added neat or as a solution in a solvent. In other embodiments, step d) I-A) is conducted at ambient temperature, and in step d) II-A), the reaction mixture is cooled, preferably to between about −10° C. and 0° C., and then the compound of formula (V) is added neat or as a solution in a solvent. In some embodiments, step d) I-A) is conducted at ambient temperature, and then the compound of formula (V) is added neat or as a solution in a solvent at ambient temperature in step d) II-A). In some embodiments, following the addition of the compound of formula (V), the reaction mixture is allowed to warm to ambient temperature.

In some other embodiments, the sulfamoylating step d) comprises the steps:
I-B) treating the compound of formula (V) with a base;
II-B) treating the reaction mixture formed in step I-B) with a solution of R″NHS(O)$_2$Cl, wherein R″ is hydrogen or an acid-labile protecting group; and III-B) optionally treating the reaction mixture formed in step III-B) with an acid.

Steps d) I-B), II-B) and III-B) may be conveniently carried out in the presence of a suitable solvent or diluent, which may be the same or different for each of steps d) I-B), II-B) and III-B). Examples of suitable solvents are as described above for steps d) I-A), II-A) and III-A).

The base in step d) I-B), is a strong base. Examples of strong bases include, but are not limited to, n-butyl lithium, tert-butyl lithium, lithium diisopropylamide, potassium diisopropylamide, lithium hexamethyldisilazane, potassium hexamethyldisilazane, sodium hexamethyldisilazane and potassium tert-butoxide.

In compounds of formula $R^uNHS(O)_2Cl$, $R^u$ is hydrogen or an amine protecting group. In some embodiments, $R^u$ is hydrogen. In other embodiments, $R^u$ is an acid-labile protecting group. In certain particular embodiments, $R^u$ is —C(O)N(Ph)$_2$. In other particular embodiments, $R^u$ is —C(O)OC(R$^v$)$_2$(R$^w$), wherein each R$^v$ is independently selected from optionally substituted $C_{1-10}$ aliphatic or optionally substituted aryl, and R$^w$ is optionally substituted $C_{1-10}$ aliphatic or optionally substituted aryl. In some other particular embodiments, $R^u$ is —C(O)OC(R$^v$)$_2$(R$^w$), wherein each R$^v$ is independently selected from hydrogen or optionally substituted $C_{1-10}$ aliphatic, and R$^w$ is optionally substituted $C_{1-10}$ aliphatic or optionally substituted aryl. In yet some other particular embodiments, $R^u$ is —C(O)OC(R$^v$)$_2$(R$^w$), wherein one R$^v$ is optionally substituted $C_{1-10}$ aliphatic, and the other R$^v$ is taken together with R$^w$ to form an optionally substituted $C_{3-6}$ cycloaliphatic ring.

In some embodiments, R$^w$ is methyl or phenyl. In some embodiments, each R$^v$ independently is methyl, ethyl, butyl, hexyl, octyl or phenyl. In some other embodiments, each R$^v$ independently is hydrogen, methyl or ethyl. In some other embodiments, one R$^v$ taken together with R$^w$ is cyclopropyl, or cyclohexyl. In preferred embodiments, $R^u$ is —C(O)OCMe$_3$, —C(O)OC(Me)$_2$Ph, —C(O)OC(Et)$_2$Ph or —C(O)OC(octyl)$_2$Ph. In other preferred embodiments, $R^u$ is —C(O)OCH$_2$Ph or —C(O)OCH(Me)Ph. In yet other preferred embodiments, $R^u$ is C(O)OC(Me)$_2$Et,

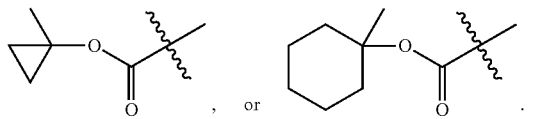

In certain preferred embodiments, $R^u$ is selected from the group consisting of —C(O)OCMe$_3$, —C(O)OCH$_2$Ph, —C(O)OCH(Me)Ph, C(O)OC(Me)$_2$Et,

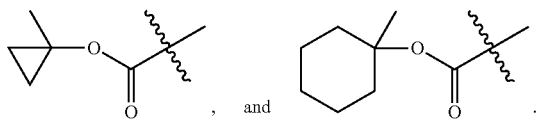

In some other embodiments, the sulfamoylating step d) comprises the steps:
I-C) treating the compound of formula (V) with a sulfamoylating reagent $R^uN^-$—$S(O)_2X^+$ and an acid; and
II-C) optionally treating the reaction mixture formed in I-C) with an acid; wherein $R^u$ has the values and preferred values as described above.

In compounds of formula $R^uN^-$—$S(O)_2X^+$, X is a tertiary amine or a nitrogen-containing heteroaryl. In some embodiments, X is a tertiary amine. Examples of suitable tertiary amines include, but are not limited to, trimethylamine, triethylamine, triethylenediamine, diazabicyclo[5.4.0]undec-7-ene (DBU), 1,4-diazabicyclo[2.2.2]octane, 1,5-diazabicycle[4.3.0]non-5-ene, sparteine, and N,N'diisopropylethylamine. Other examples of suitable tertiary amines include, but are not limited to, tributylamine, 1-azabicyclo[2.2.2]octane, N,N'-dimethylpiperazine, N-ethylmorpholine, and tripropylamine.

In some other embodiments, X is a nitrogen-containing heteroaryl. Examples of suitable nitrogen-containing heteroaryl include, but are not limited to, unsubstituted or substituted pyridine, unsubstituted or substituted imidazole, and unsubstituted or substituted pyrrole.

In some other embodiments, X is a pyridine or a substituted pyridine. Examples of pyridines or substituted pyridines include, but are not limited to, pyridine, collidine, 2,6-lutidine, 4-dimethylaminopyridine, 2,6-di-tert-butylpyridine and 2,6-di-tert-butyl-4-methylpyridine.

In preferred embodiments, X is selected from the group consisting of triethylamine, triethylenediamine, 1-azabicyclo[2.2.2]octane, N,N'-dimethylpiperazine, N-ethylmorpholine and pyridine. In certain preferred embodiments, X is triethylenediamine.

Steps d) I-C) and II-C) may be conveniently carried out in the presence of a suitable solvent or diluent. Examples of suitable solvents are as described above for steps d) I-A), II-A) and III-A).

The acid used in step d) I-C) may be a mineral acid or an organic acid. Examples of mineral acids include but are not limited to hydrochloric acid, sulfuric acid, hydrobromic acid, nitric acid and phosphoric acid. Examples of organic acids include but are not limited to acetic acid, propionic acid, isobutyric acid, benzoic acid, formic acid, oxalic acid, trichloroacetic acid, trifluoroacetic acid, methanesulfonic acid, p-toluensulfonic acid and trifluoromethanesulfonic acid.

In some embodiments, in step d) I-C) the treating is carried out at such a rate to keep the reaction temperature below about 10° C. In some embodiments, in step d) I-C), the treating is carried out at ambient temperature. In some other embodiments, in step d) I-C), the reaction mixture is treated with additional portions of the sulfamoylating reagent and acid until the reaction is complete. In some such embodiments, the treating with additional portions is carried out at room temperature. In other such embodiments, the treating with additional portions is carried out at reaction temperatures below about 10° C.

In some embodiments, the sulfamoylating step d) comprises the steps:
I-D) treating the compound of formula (V) with a sulfamoylating reagent $R^uN^-$—$S(O)_2X^+$; and
II-D) optionally treating the reaction mixture formed in step d) I-D) with an acid;
wherein $R^u$ and X have the values and preferred values as described above.

In some embodiments, the treating of step d) I-D) occurs when the compound of formula (V) and the compound of formula $R^uN^-$—$S(O)_2X^+$ are mixed together, and then a suitable solvent or diluent is added. In some other embodiments, the treating of step d) I-D) occurs when the compound of formula $R^uN^-$—$S(O)_2X^+$ is added to the compound of formula (V) in a suitable solvent or diluent. In yet some other embodiments, the treating of step d) I-D) occurs when the compound of formula (V) is added to the compound of formula R$^u$N$^-$—S(O)$_2$X$^+$ in a suitable solvent or diluent.

Steps d) I-D) and II-D) may be conveniently carried out in the presence of a suitable solvent or diluent, which may be the same or different for each of steps d) I-D), and II-D). Examples of suitable solvents are as described above for steps d) I-A), II-A) and III-A). In some embodiments, steps d) I-D) and II-D) are carried out in a solvent comprising acetonitrile, N,N'-dimethylacetamide, N,N'-dimethylformamide, N-methylpyrrolidinone, dimethylsulfoxide, or mixtures thereof.

The treating of step d) I-D) is preferably performed at ambient or elevated reaction temperature. One skilled in the art will be able to select a suitable reaction temperature and reaction time in view of the reaction conditions being used.

In some embodiments, step d) I-D) may be carried out at reaction temperatures of at least about 0° C., 25° C. or 40° C. In some embodiments, step d) I-D) may be carried out at reaction temperatures no greater than 55° C., 65° C. or 95° C. Any range encompassing these high and low reaction temperatures are included within the scope of the invention. Step d) I-D) is preferably performed at reaction temperatures in the range of about 0° C. to about 95° C., about 25° C. to about 65° C., or about 40° C. to about 55° C.

Preferably, the process for forming a compound of formula (VI) from a compound of formula (V) comprising steps d) I-D) and II-D is characterized by at least one of the following features:
(i) the treating of step d) I-D) is carried out in acetonitrile; and
(ii) the treating of d) I-D) is performed at a reaction temperature in the range of about 40° C. to about 55° C.

In some embodiments, the compound of formula R$^u$N$^-$—S(O)$_2$X$^+$ is formed in situ prior to the treating step d) I-C) or step d) I-D).

In some other embodiments, the compound of formula R$^u$N$^-$—S(O)$_2$X$^+$ is isolated prior to its use in step d) I-C) or step d) I-D). In some such embodiments, formation of the compound of formula R$^u$N$^-$—S(O)$_2$X$^+$, wherein R$^u$ is —C(O)OC(R$^v$)$_2$(R$^w$), comprises the following steps:
I-E) treating (R$^w$)(R$^v$)$_2$C—OH with chlorosulfonylisocyanate;
II-E) treating the reaction mixture formed in step I-E) with X; and
III-E) isolating the sulfamoylating reagent R$^u$NS(O)$_2-$X$^+$;
wherein R$^v$, R$^w$, and X have the values and preferred values as described above.

Steps I-E), II-E) and III-E) may be conveniently carried out in the presence of a suitable solvent or diluent. Examples of suitable solvents are as described above for steps d) I-A), II-A) and III-A).

In some embodiments, in step I-E) the chlorosulfonylisocyanate is added to a cooled solution of (R$^w$)(R$^v$)$_2$C—OH in a suitable solvent at such a rate to keep the temperature below about 10° C. In some embodiments, in step I-E), (R$^w$)(R$^v$)$_2$C—OH is added to a cooled solution of the chlorosulfonylisocyanate in a suitable solvent at such a rate to keep the temperature below about 15° C. In some embodiments, in step II-E), X is added to the reaction mixture formed in step I-E), at such a rate to keep the temperature below about 15° C. In some embodiments, the sulfamoylating reagent is isolated by concentrating the reaction mixture. In some other embodiments, the sulfamoylating reagent is isolated by concentrating the reaction mixture of step III-E), and then stirring the residue in a different solvent such that a solid precipitate is formed which can be collected by filtration and dried. In some embodiments, the sulfamoylating reagent is directly isolated in step III-E), by filtration from the reaction mixture of step II-E).

In some embodiments, the compound of formula R$^u$N$^-$—S(O)$_2$X$^+$, is isolated as a complex further comprising the hydrochloride salt of X. In some embodiments, the ratio of the compound of formula R$^u$N$^-$—S(O)$_2$X$^+$ to the hydrochloride salt of X in the complex is less than one. In some other embodiments, the ratio of the compound of formula R$^u$N$^-$—S(O)$_2$X$^+$ to the hydrochloride salt of X in the complex is about one. In some other embodiments, the ratio of the compound of formula R$^u$N$^-$—S(O)$_2$X$^+$ to the hydrochloride salt of X in the complex is more than one.

In some embodiments, when R$^u$ is hydrogen, the compound of formula (VI) can be directly isolated and optionally purified following step d) II-A) or step d) II-B) by methods known to one of skill in the art.

In other embodiments when R$^u$ is an acid-labile protecting group, the reaction mixture is treated with an acid in step d) III-A) or step d) III-B) or step d) II-C) or step d) II-D). Mineral acids, Lewis acids, and organic acids all are suitable for use in the reaction. Examples of mineral acids include, but are not limited to, hydrochloric acid, sulfuric acid, hydrobromic acid, nitric acid and phosphoric acid. Examples of suitable Lewis acids include, but are not limited to, SnCl$_4$, (CH$_3$)$_3$SiI, Mg(C$_{104}$)$_2$, BF$_3$, ZnBr$_2$, Sn(OTf)$_2$, and Ti(Oi Pr)$_4$. Examples of organic acids include but are not limited to acetic acid, propionic acid, benzoic acid, formic acid, oxalic acid, trichloroacetic acid, trifluoroacetic acid, methanesulfonic acid, p-toluensulfonic acid and trifluoromethanesulfonic acid.

In some other embodiments, when R$^u$ is an acid-labile protecting group, a compound characterized by formula (VIa), wherein each of variables R$^a$, R$^b$, R$^c$, R$^d$, R$^e$, R$^{e'}$, R$^f$, R$^h$, R$^{h'}$, R$^k$, R$^m$, R$^n$, and R$^o$ in formula (VIa) is as defined above in formula (VI), can be directly isolated, and optionally purified, following step d) II-A) or step d) II-B) or step d) I-C) or step d) I-D), by methods known to one of skill in the art. The compound of formula (VIa) can then be treated in a separate reaction with an acid to remove the protecting group R$^u$ using the same reactions conditions as described herein for step d) III-A) or step d) III-B) or step d) II-C) or step d) II-D), to afford the compound of formula (VI). It will be recognized by one of skill in the art, that when R$^u$ in compounds of formula (VIa) is an acid-labile protecting group, there may be alternative deprotection conditions that will remove the R$^u$ group to generate compounds of formula (VI).

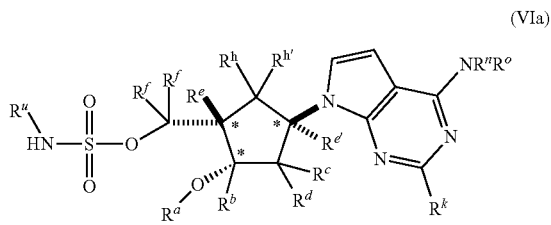

(VIa)

In some embodiments, wherein R$^u$ is an acid labile protecting group, following removal of the acid-labile protecting group by treatment with acid, the reaction mixture is neutralized during work-up, and the compound of formula (VI) is isolated as a free base. In such embodiments, the compound of formula (VI) can be isolated as a solid following the work-up by concentration of the solvent or diluent, and treatment with methylene chloride, trifluorotoluene, or mixtures thereof. The resulting solid can be isolated by filtration. In some other embodiments, the compound of formula (VI) may be isolated as a salt.

In some other embodiments, when $R^u$ is an amine protecting group, a compound characterized by formula (VIa) wherein each of variables $R^a$, $R^b$, $R^c$, $R^d$, $R^e$, $R^{e'}$, $R^f$, $R^h$, $R^{h'}$, $R^k$, $R^m$, $R^n$, and $R^o$ in formula (VIa) is as defined above in formula (VI), can be directly isolated, and optionally purified, following step d) II-A) or step d) II-B) or step d) I-C) or step d) I-D), by methods known to one of skill in the art. The compound of formula (VIa) can then be converted to the compound of formula (VI) by removal of the amine protecting group $R^u$, by methods known to one of the skill in the art.

With respect to the compounds and the processes described herein, the following preferred values are applicable.

In formulas (I), (Ia), (II), (IIa), (IV), (V) and (VI), each of $R^b$, $R^h$ and $R^{h'}$ is independently hydrogen, fluoro, $C_{1-4}$ aliphatic or $C_{1-4}$ fluoroaliphatic. In some embodiments, each of $R^b$, $R^h$ and $R^{h'}$ is independently hydrogen, fluoro, methyl, ethyl or trifluoromethyl. In preferred embodiments, each of $R^b$, $R^h$ and $R^{h'}$ is hydrogen.

In formulas (I), (Ia), (II), (IV), (V) and (VI), $R^d$ is hydrogen, fluoro, $C_{1-4}$ aliphatic or $C_{1-4}$ fluoroaliphatic. In some embodiments, $R^d$ is hydrogen, fluoro, methyl, ethyl or trifluoromethyl. In preferred embodiments, $R^d$ is hydrogen.

In formula (IIa), $R^{d'}$ is hydrogen, fluoro, bromo, $C_{1-4}$ aliphatic or $C_{1-4}$ fluoroaliphatic. In some embodiments, $R^{d'}$ is hydrogen, fluoro, methyl, ethyl or trifluoromethyl. In other embodiments, $R^{d'}$ is hydrogen or bromo. In some preferred embodiments, $R^{d'}$ is hydrogen. In some other preferred embodiments, $R^{d'}$ is bromo.

In formulas (I), (Ia), (II), (IV), (V) and (VI), each $R^f$ independently is hydrogen, fluoro, $C_{1-4}$ aliphatic or $C_{1-4}$ fluoroaliphatic. In some embodiments, each $R^f$ is independently hydrogen, fluoro, methyl, ethyl or trifluoromethyl. In preferred embodiments, each $R^f$ is hydrogen.

In formulas (I), (Ia), (II), (IIa), (IV), (V), (VI), each of $R^e$ and $R^{e'}$ is independently hydrogen or $C_{1-4}$ aliphatic. In some embodiments, each of $R^e$ and $R^{e'}$ is independently hydrogen, methyl or ethyl. In preferred embodiments, each of $R^e$ and $R^{e'}$ is hydrogen.

In formulas (I), (Ia), (III), (IV), (V) and (VI), $R^k$ is hydrogen or $C_{1-4}$ aliphatic. In some embodiments, $R^k$ is hydrogen, methyl or ethyl. In preferred embodiments, $R^k$ is hydrogen.

In formulas (I), (Ia), (II), (IIa), (IV), (V) and (VI), $R^c$ is hydrogen, fluoro, chloro, —OH, —O—$R^m$ or optionally substituted $C_{1-4}$ aliphatic. In some embodiments, $R^c$ is hydrogen, —OH, fluoro or methyl. In preferred embodiments, $R^c$ is hydrogen, —OH or —O—$R^m$. In more preferred embodiments, $R^c$ is hydrogen or —OH. In other more preferred embodiments, $R^c$ is hydrogen.

In formulas (I), (Ia), (II), (IIa), (IV), (V) and (VI), $R^a$ and $R^j$ are each independently hydrogen or a hydroxyl protecting group, and $R^m$ is a hydroxyl protecting group. $R^a$ may be taken together with $R^j$ and the intervening atoms to form a cyclic diol protecting group, or $R^a$ may be taken together with $R^m$ and the intervening atoms to form a cyclic diol protecting group, or $R^j$ may be taken together with $R^m$ to form a cyclic diol protecting group. Preferred values for hydroxyl protecting groups and cyclic diol protecting groups are given below.

In some embodiments, $R^a$ is hydrogen. In some embodiments $R^j$ is hydrogen. In certain particular embodiments both $R^a$ and $R^j$ are hydrogen.

In some embodiments, the hydroxyl protecting group is selected from the group consisting of a silyl protecting group, optionally substituted aliphatic, —C(O)—$R^{aa}$ and —C(O)—O—$R^{aa}$, where $R^{aa}$ is optionally substituted $C_{1-4}$ aliphatic or optionally substituted aryl.

In some embodiments, the silyl protecting group is selected from trimethylsilyl (TMS), triethylsilyl (TES), triisopropylsilyl (TIPS), tert-butyldimethylsilyl (TBDMS) and tert-butyldiphenylsilyl (TBDPS). In some embodiments, the optionally substituted $C_{1-4}$ aliphatic protecting group is selected from methoxymethyl, benzyl (Bn), p-methoxybenzyl (PMB), 9-fluorenylmethyl (Fm), diphenylmethyl (benzhydryl, DPM) and the like. In some embodiments, the —C(O)—$R^{aa}$ protecting group is selected from acetyl, formyl, pivaloyl, benzoyl and the like. In some embodiments, the —C(O)—O—$R^{aa}$ protecting group is selected from benzyloxycarbonyl (Cbz), methoxycarbonyl, tert-butoxycarbonyl (t-Boc), fluorenylmethoxycarbonyl (Fmoc) and the like.

In some embodiments, the cyclic diol protecting group is a 1,2-cyclic diol protecting group. In some embodiments, the cyclic diol protecting group is a 1,3-cyclic diol protecting group. In some other embodiments, the cyclic diol protecting group is —C($R^{aa}$)($R^{bb}$)—, where $R^{aa}$ is optionally substituted $C_{1-4}$ aliphatic or optionally substituted aryl, and $R^{bb}$ is hydrogen or optionally substituted $C_{1-4}$ aliphatic. In some preferred embodiments, $R^{aa}$ is hydrogen or methyl. In some preferred embodiments, $R^{bb}$ is methyl, phenyl or 4-methoxyphenyl.

In formulas (I), (II) and (IV), $R^g$ is chloro, fluoro, iodo or bromo. In some preferred embodiments, $R^g$ is chloro or fluoro. In certain preferred embodiments, $R^g$ is chloro.

In formula (Ia), $R^{g'}$ is halogen, —O—$R^s$, —S—$R^t$, —S(O)$R^t$ or —S(O)$_2R^t$; wherein $R^s$ is $C_{1-4}$ aliphatic, alkylsulphonyl, fluoroalkylsulphonyl, optionally substituted aryl or optionally substituted arylsulphonyl, and $R^t$ is optionally substituted $C_{1-4}$ aliphatic or optionally substituted aryl. In some embodiments, $R^{g'}$ is chloro, fluoro, iodo, methoxy, ethoxy, substituted or unsubstituted phenoxy, mesylate (—OSO$_2$CH$_3$), tosylate (—OSO$_2$C$_6$H$_4$CH$_3$), triflate (—OSO$_2$CF$_3$), methylsulfonyl and benzylsulfonyl. In preferred embodiments, $R^{g'}$ is chloro, fluoro, bromo, mesylate, tosylate or triflate.

In formulas (II) and (IV), $R^l$ is —CH$_2$—CHO or —CH$_2$CH(OR$^{l'}$)$_2$, wherein each $R^{l'}$ is independently $C_{1-6}$ aliphatic, or two $R^{l'}$ are taken together with the intervening oxygen and carbon atoms to form an optionally substituted 5- or 6-membered cyclic acetal moiety. In some embodiments, two $R^{l'}$ are taken together with the intervening oxygen and carbon atoms to form an optionally substituted 5- or 6-membered cyclic acetal moiety. In some such embodiments, two $R^{l'}$, taken together with the intervening oxygen and carbon atoms, form an optionally substituted 1,3-dioxane or 1,3-dioxolane moiety. In some other embodiments each $R^{l'}$ independently is $C_{1-3}$ aliphatic. In certain particular embodiments each $R^{l'}$ is methyl or ethyl.

In amines of formula HNR$^n$R$^o$ and in compounds of formulas (V) and (VI), $R^n$ is hydrogen or $C_{1-4}$ aliphatic. In some embodiments, $R^n$ is hydrogen, methyl or ethyl. In preferred embodiments, $R^n$ is hydrogen.

In amines of formula HNR$^n$R$^o$, and in formulas (V) and (VI), $R^o$ is optionally substituted $C_{1-10}$ aliphatic, aryl, heteroaryl or heterocyclic. In some embodiments, $R^o$ is optionally substituted $C_{1-10}$ aliphatic. In some embodiments, $R^o$ is an optionally substituted cycloaliphatic or heterocyclic ring. In other embodiments, $R^o$ is an aryl or heteroaryl ring. In certain embodiments, $R^o$ is a mono-, bi- or tricyclic ring system. In some other certain embodiments, $R^o$ is a mono- or bicyclic ring system.

In some such embodiments, the ring represented by $R^o$ is selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, indolyl, isoindolyl, indazolyl, benzimidazolyl, benzthiazolyl, benzothienyl, benzofuranyl, purinyl, quinolyl, isoquinolyl, cinnolinyl, phthalazinyl, quinazolinyl, quinoxalinyl, naphthyridinyl, pteridinyl, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, quinuclidinyl, tetrahydroquinolinyl, tetrahydroisoquinolinyl, indanyl, phenanthridinyl, tetrahydronaphthyl, indolinyl, benzodioxanyl, benzodioxolyl, chromanyl, cyclopropyl, cyclobutyl, cyclopentyl, cyclopentenyl, cyclohexyl, cyclohexenyl, cycloheptyl, cycloheptenyl, cyclooctyl, cyclooctenyl, cyclooctadienyl, bicycloheptenyl and bicyclooctanyl. In certain embodiments, the ring represented by $R^o$ is an optionally substituted indanyl, tetrahydronaphthyl, or chromanyl.

In such embodiments, the ring or ring system represented by $R^o$ may be optionally substituted on either or both of its component rings and the substitutents may be the same or different. In particular, each substitutable unsaturated ring carbon is unsubstituted or substituted with 0-2 $R^p$ and each substitutable saturated ring carbon is unsubstituted or substituted with 0-2 $R^q$. The variables $R^p$ and $R^q$ have the values described below.

Each $R^p$ independently is selected from the group consisting of fluoro, —$OR^{5x}$, —$N(R^{4x})(R^{4y})$, —$CO_2R^{5x}$, or —$C(O)N(R^{4x})(R^{4y})$, or a $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$.

Each $R^q$ independently is selected from the group consisting of fluoro, —$OR^{5x}$, —$N(R^{4x})(R^{4y})$, —$CO_2R^{5x}$, or —$C(O)N(R^{4x})(R^{4y})$, or a $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$, provided that when two $R^q$ are attached to the same carbon atom, one must be selected from the group consisting of fluoro, —$CO_2R^{5x}$, —$C(O)N(R^{4x})(R^{4y})$, and $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$; or two $R^q$ on the same carbon atom together form =O or =$C(R^{5x})_2$.

$R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted, and $R^{4y}$ is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S. Each $R^{5x}$ independently is hydrogen, $C_{1-4}$ alkyl, $C_{1-4}$ fluoroalkyl, or an optionally substituted $C_{6-10}$ aryl or $C_{6-10}$ ar($C_{1-4}$)alkyl.

In some embodiments, in amines of formula $HNR''R^o$, and in formulas (V), (VI), (VIa) and (VIb) the ring or ring system represented by $R^o$ is represented by formula (VII):

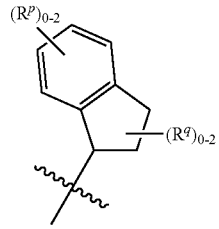

(VII)

wherein, the variables $R^p$ and $R^q$ have the values described above.

In some other embodiments, in amines of formula $HNR''R^o$ and in formulas (V), (Va), (VI), (VIa), (VIb), (VIc) and (VId), the ring or ring system represented by $R^o$ is selected from the group consisting of:

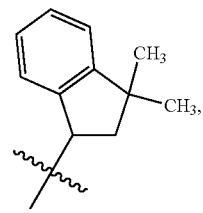

(VII)-i

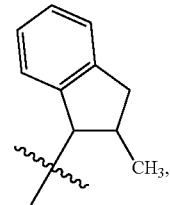

(VII)-ii

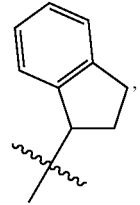

(VII)-iii

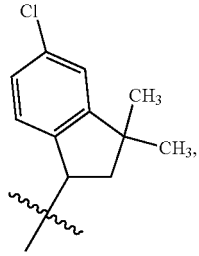

(VII)-iv

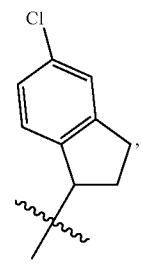

(VII)-v (VII)-vi
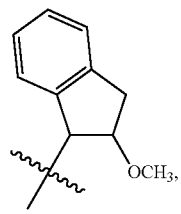
(VII)-vii
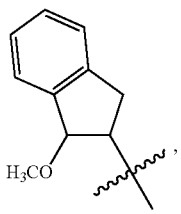
(VII)-viii
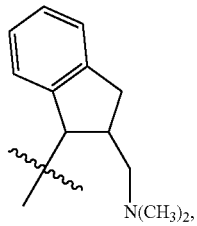
(VII)-ix
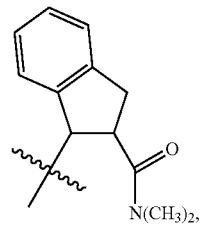
(VII)-x
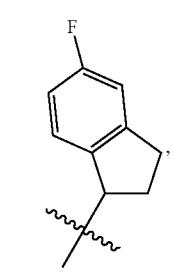
(VII)-xi
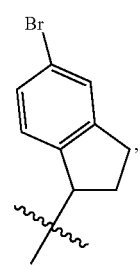
(VII)-xii
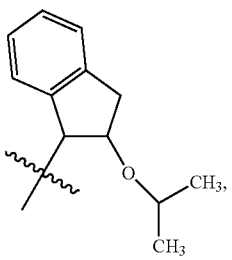
(VII)-xiii
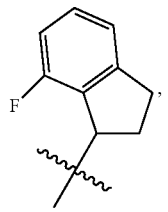
(VII)-xiv
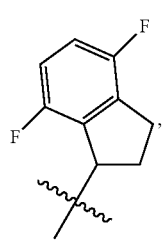
(VII)-xv
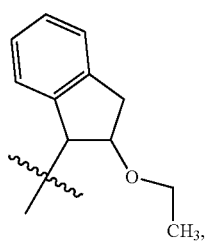
(VII)-xvi
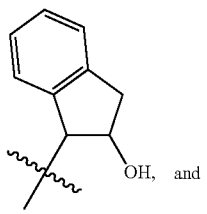
and
(VII)-xvii
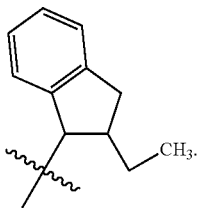
In certain particular embodiments, in amines of formula HNR″R° and in formulas (V), (Va), (VI), (VIa), (VIb), (VIc) and (VId), the ring or ring system represented by R° is selected from the group consisting of:

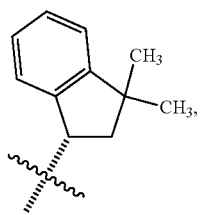 (VII)-xviii
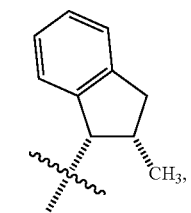 (VII)-xix
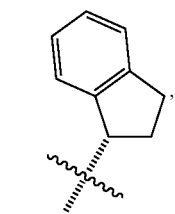 (VII)-xx
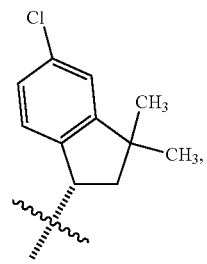 (VII)-xxi
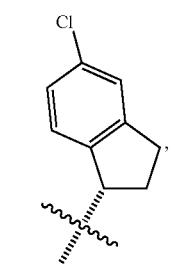 (VII)-xxii
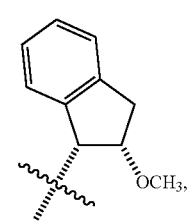 (VII)-xxiii
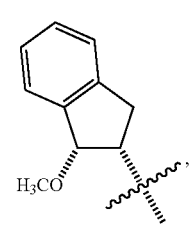 (VII)-xxiv
-continued
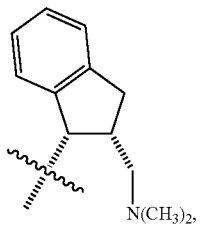 (VII)-xxv
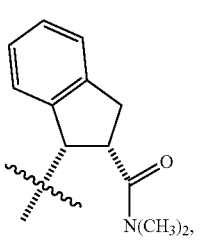 (VII)-xxvi
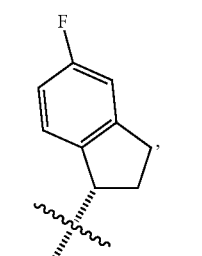 (VII)-xxvii
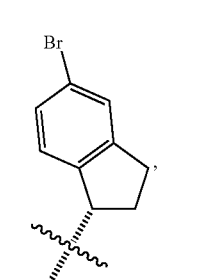 (VII)-xxviii
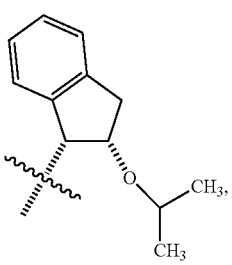 (VII)-xxix
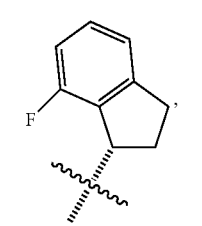 (VII)-xxx

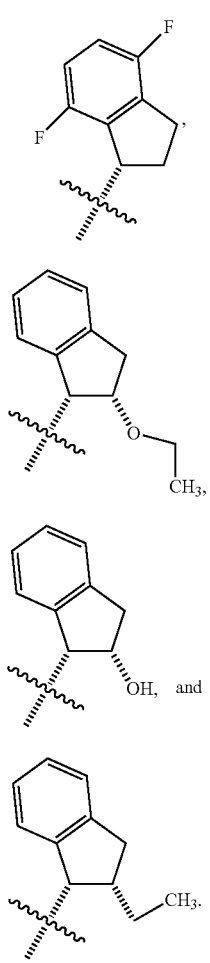

(VII)-xxxi (VII)-xxxii (VII)-xxxiii (VII)-xxxiv

In a particular embodiment, the invention relates to a process for the formation of a subgenus of the compounds of formula (VI), characterized by formula (VIb):

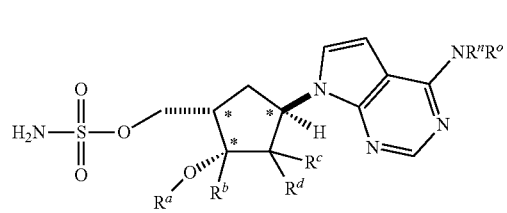

(VIb)

or a pharmaceutically acceptable salt thereof; wherein:
stereochemical configurations depicted at asterisk positions indicate relative stereochemistry;
the variables $R^a$, $R^b$, $R^c$, $R^d$, $R^n$, and $R^o$ have the values and preferred values described above for formulas (I)-(VI); and
the process comprises steps (a)-(d) as described above for the formation of compounds of formula (VI). Preferred conditions for each of steps (a)-(d) are as described above for the formation of compounds of formulas (I)-(VI).

In another particular embodiment, the invention relates to a process for the formation of a subgenus of the compounds of formula (VI), characterized by formula (VIc):

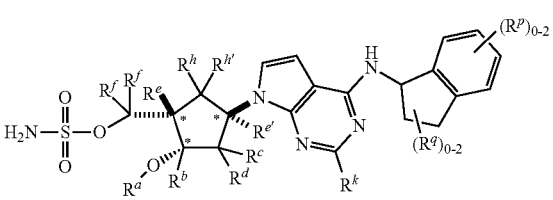

(VIc)

or a pharmaceutically acceptable salt thereof; wherein:
stereochemical configurations depicted at asterisk positions indicate relative stereochemistry;
the variables $R^a$, $R^b$, $R^c$, $R^d$, $R^p$, and $R^q$ have the values and preferred values described above for formulas (I)-(VI); and
the process comprises steps a)-d) as described above for the formation of compounds of formula (VI). Preferred conditions for each of steps a)-d) are as described above for the formation of compounds of formulas (I)-(VI).

In another particular embodiment, the invention relates to a process for the formation of a subgenus of the compounds of formula (VI), characterized by formula (VId):

(VId)

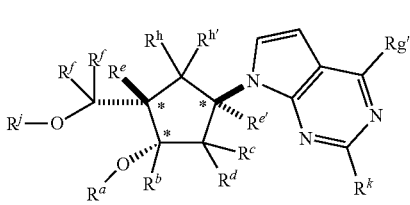

or a pharmaceutically acceptable salt thereof; wherein:
stereochemical configurations depicted at asterisk positions indicate relative stereochemistry;
the variables $R^a$, $R^b$, $R^c$, $R^d$, $R^e$, $R^{e'}$, $R^f$, $R^h$, $R^{h'}$, $R^k$, $R^p$, and $R^q$ have the values and preferred values described above for formulas (I)-(VII); and
the process comprises steps a)-d) as described above for the formation of compounds of formula (VI). Preferred conditions for each of steps a)-d) are as described above for the formation of compounds of formulas (I)-(VI).

Another aspect of the invention relates to compounds which are useful intermediates in the processes described above, such as compounds of formula (Ia) and formula (IIa).

One embodiment relates to compounds of formula (Ia):

(Ia)

or a salt thereof;
wherein stereochemical configurations depicted at asterisk positions indicate absolute stereochemistry;
$R^a$ is hydrogen or a protecting group; or $R^a$ taken together with $R^j$ and the intervening atoms forms a cyclic diol protecting group; or $R^a$ taken together with $R^m$ and the intervening atoms forms a cyclic diol protecting group;

$R^b$ is hydrogen, fluoro, $C_{1-4}$ aliphatic or $C_{1-4}$ fluoroaliphatic;

$R^c$ is hydrogen, fluoro, chloro, —OH, —O—$R^m$ or optionally substituted $C_{1-4}$ aliphatic;

$R^d$ is hydrogen, fluoro, $C_{1-4}$ aliphatic or $C_{1-4}$ fluoroaliphatic;

$R^e$ is hydrogen or $C_{1-4}$ aliphatic;

$R^{e'}$ is hydrogen or $C_{1-4}$ aliphatic;

each $R^f$ is independently hydrogen, fluoro, $C_{1-4}$ aliphatic or $C_{1-4}$ fluoroaliphatic;

$R^{g'}$ is a leaving group;

$R^h$ is hydrogen, fluoro, $C_{1-4}$ aliphatic, or $C_{1-4}$ fluoroaliphatic;

$R^{h'}$ is hydrogen, fluoro, $C_{1-4}$ aliphatic, or $C_{1-4}$ fluoroaliphatic;

$R^j$ is hydrogen or a hydroxyl protecting group; or $R^j$ taken together with $R^a$ and the intervening atoms forms a cyclic diol protecting group;

$R^k$ is hydrogen or $C_{1-4}$ aliphatic; and $R^m$ is a hydroxyl protecting group; or $R^m$ taken together with $R^a$ and the intervening atoms forms a cyclic diol protecting group.

In some embodiments, the compound of formula (Ia) is characterized by formula (Iaa):

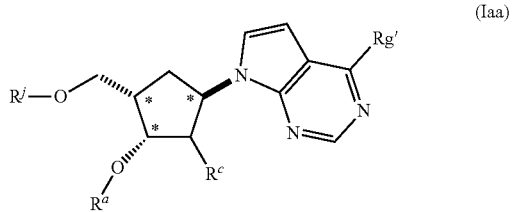

(Iaa)

wherein stereochemical configurations depicted at asterisk positions indicate absolute stereochemistry;

$R^{g'}$ is chloro, bromo, fluoro, iodo, —O—$R^s$, —S—$R^t$, —S(O)$R^t$ or —S(O)$_2R^t$;

wherein $R^s$ is $C_{1-4}$ aliphatic, alkylsulphonyl, fluoroalkylsulphonyl, optionally substituted aryl or optionally substituted arylsulphonyl; and $R^t$ is optionally substituted $C_{1-4}$ aliphatic or optionally substituted aryl.

In certain embodiments, the compound of formula (Ia) is characterized by formula (Iaa) wherein $R^c$ is hydrogen, —OH or —O—$R^m$;

$R^a$ is hydrogen or a hydroxyl protecting group selected from the group consisting of a silyl protecting group, optionally substituted aliphatic, —C(O)—$R^{aa}$ and —C(O)—O—$R^{aa}$, or $R^a$ taken together with $R^j$ and the intervening atoms forms a cyclic diol protecting group —C($R^{aa}$)($R^{bb}$)—; or $R^a$ taken together with $R^m$ and the intervening atoms forms a cyclic diol protecting group —C($R^{aa}$)($R^{bb}$)—;

$R^j$ is hydrogen or a hydroxyl protecting group selected from the group consisting of a silyl protecting group, optionally substituted aliphatic, —C(O)—$R^{aa}$ and —C(O)—O—$R^{aa}$; or $R^j$ taken together with $R^a$ and the intervening atoms forms a cyclic diol protecting group —C($R^{aa}$)($R^{bb}$)—;

$R^m$ is a hydroxyl protecting group selected from the group consisting of a silyl protecting group, optionally substituted aliphatic, —C(O)—$R^{aa}$ and —C(O)—O—$R^{aa}$; or $R^m$ taken together with $R^a$ and the intervening atoms forms a cyclic diol protecting group —C($R^{aa}$)($R^{bb}$)—;

$R^{aa}$ is optionally substituted $C_{1-4}$ aliphatic or optionally substituted aryl; and $R^{bb}$ is hydrogen or optionally substituted $C_{1-4}$ aliphatic.

In certain other preferred embodiments, the compound of formula (Ia) is characterized by formula (Iaa) and values and preferred values for $R^a$, $R^j$, $R^m$, $R^c$, and $R^{g'}$ are as described above.

Another aspect of this invention relates to compounds of formula (IIa):

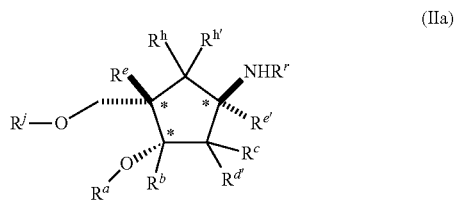

(IIa)

or a salt thereof; wherein:

stereochemical configurations depicted at asterisk positions indicates absolute stereochemistry;

$R^a$ is hydrogen or a protecting group; or $R^a$ taken together with $R^j$ and the intervening atoms forms a cyclic diol protecting group; or $R^a$ taken together with $R^m$ and the intervening atoms forms a cyclic diol protecting group;

$R^b$ is hydrogen, fluoro, $C_{1-4}$ aliphatic or $C_{1-4}$ fluoroaliphatic;

$R^c$ is hydrogen, fluoro, chloro, —OH, —O—$R^m$ or optionally substituted $C_{1-4}$ aliphatic;

$R^{d'}$ is hydrogen, fluoro, bromo, $C_{1-4}$ aliphatic or $C_{1-4}$ fluoroaliphatic;

$R^e$ is hydrogen or $C_{1-4}$ aliphatic;

$R^{e'}$ is hydrogen or $C_{1-4}$ aliphatic;

$R^h$ is hydrogen, fluoro, $C_{1-4}$ aliphatic, or $C_{1-4}$ fluoroaliphatic;

$R^{h'}$ is hydrogen, fluoro, $C_{1-4}$ aliphatic, or $C_{1-4}$ fluoroaliphatic;

$R^j$ is hydrogen or a hydroxyl protecting group; or $R^j$ taken together with $R^a$ and the intervening atoms forms a cyclic diol protecting group;

$R^m$ is a hydroxyl protecting group; or $R^m$ taken together with $R^a$ and the intervening carbon atoms forms a cyclic diol protecting group; and $R^r$ is hydrogen or an amine protecting group.

In some embodiments, the compound of formula (IIa) is characterized by formula (IIaa):

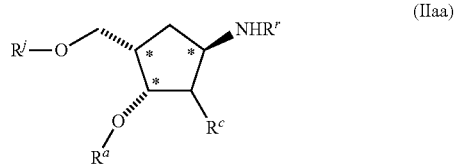

(IIaa)

wherein, stereochemical configurations depicted at asterisk positions indicate absolute stereochemistry; and $R^c$ is hydrogen, —OH or —O—$R^m$;

$R^a$ is hydrogen or a hydroxyl protecting group selected from the group consisting of a silyl protecting group, optionally substituted aliphatic, —C(O)—$R^{aa}$ and —C(O)—O—$R^{aa}$, or $R^a$ taken together with $R^j$ and the intervening atoms forms a cyclic diol protecting group —C($R^{aa}$)($R^{bb}$)—; or $R^a$ taken together with $R^m$ and the intervening atoms forms a cyclic diol protecting group —C($R^{aa}$)($R^{bb}$)—;

$R^j$ is hydrogen or a hydroxyl protecting group selected from the group consisting of a silyl protecting group, optionally substituted aliphatic, —C(O)—$R^{aa}$ and —C(O)—O—$R^{aa}$; or $R^j$ taken together with $R^a$ and the intervening atoms forms a cyclic diol protecting group —C($R^{aa}$)($R^{bb}$)—;

$R^m$ is a hydroxyl protecting group selected from the group consisting of a silyl protecting group, optionally substituted aliphatic, —C(O)—$R^{aa}$ and —C(O)—O—$R^{aa}$; or $R^m$ taken together with $R^a$ and the intervening atoms forms a cyclic diol protecting group —C($R^{aa}$)($R^{bb}$)—;

$R^{aa}$ is optionally substituted $C_{1-4}$ aliphatic or optionally substituted aryl;

$R^{bb}$ is hydrogen or optionally substituted $C_{1-4}$ aliphatic; and $R^r$ is hydrogen or an amine protecting group.

In some other embodiments, the compound of formula (IIa) is characterized by formula (IIbb):

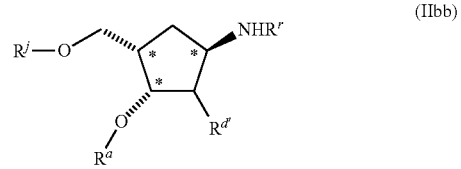

(IIbb)

wherein stereochemical configurations depicted at asterisk positions indicate absolute stereochemistry; and $R^{d'}$ is bromo;

$R^a$ is hydrogen or a hydroxyl protecting group selected from the group consisting of a silyl protecting group, optionally substituted aliphatic, —C(O)—$R^{aa}$ and —C(O)—O—$R^{aa}$, or $R^a$ taken together with $R^j$ and the intervening atoms forms a cyclic diol protecting group —C($R^{aa}$)($R^{bb}$)—; or $R^a$ taken together with $R^m$ and the intervening atoms forms a cyclic diol protecting group —C($R^{aa}$)($R^{bb}$)—;

$R^j$ is hydrogen or a hydroxyl protecting group selected from the group consisting of a silyl protecting group, optionally substituted aliphatic, —C(O)—$R^{aa}$ and —C(O)—O—$R^{aa}$; or $R^j$ taken together with $R^a$ and the intervening atoms forms a cyclic diol protecting group —C($R^{aa}$)($R^{bb}$)—;

$R^m$ is a hydroxyl protecting group selected from the group consisting of a silyl protecting group, optionally substituted aliphatic, —C(O)—$R^{aa}$ and —C(O)—O—$R^{aa}$; or $R^m$ taken together with $R^a$ and the intervening atoms forms a cyclic diol protecting group —C($R^{aa}$)($R^{bb}$)—;

$R^{aa}$ is optionally substituted $C_{1-4}$ aliphatic or optionally substituted aryl;

$R^{bb}$ is hydrogen or optionally substituted $C_{1-4}$ aliphatic; and $R^r$ is hydrogen or an amine protecting group.

In certain preferred embodiments, the compound of formula (Ia) is characterized by formulas (IIaa) and (IIbb) and values and preferred values for $R^a$, $R^j$, $R^m$, $R^c$, and $R^{d'}$ are as described above.

In formulas (IIa), (IIIaa), and (IIbb), $R^r$ is hydrogen or an amine protecting group. In some embodiments, $R^r$ is hydrogen. In other embodiments, $R^r$ is an amine protecting group selected from —C(O)$R^{cc}$, —C(O)—O$R^{cc}$, —CH$_2R^{cc}$ and —C($R^{cc}$)$_3$, wherein $R^{cc}$ is optionally substituted $C_{1-4}$ aliphatic or optionally substituted aryl. In preferred embodiments $R^r$ is hydrogen, benzyl, 4-methoxybenzyl, tert-butoxycarbonyl, triphenylmethyl or (4-methoxyphenyl)diphenylmethyl. In certain preferred embodiments, $R^r$ is tert-butoxycarbonyl or triphenylmethyl.

In particular embodiments, the invention relates to a compound selected from the group consisting of:

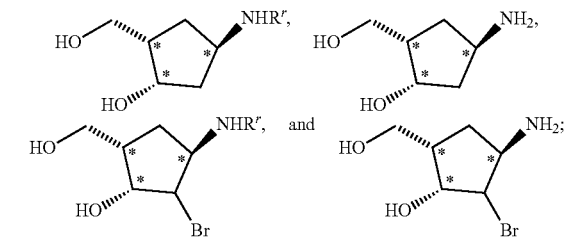

wherein stereochemical configurations depicted at asterisk positions indicate absolute stereochemistry; and $R^r$ is —C(O)$R^{cc}$, —C(O)—O$R^{cc}$, —CH$_2R^{cc}$ or —C($R^{cc}$)$_3$, wherein $R^{cc}$ is optionally substituted $C_{1-4}$ aliphatic or optionally substituted aryl.

In some embodiments the compound of formula (IIa) has a diastereoisomeric purity of at least 80%, 90%, 95% or 99%. In some other embodiments the compound of formula (IIa) has an enantiomeric purity of at least 80%, 90%, 95% or 99%.

In some embodiments, the stereochemical configurations depicted at asterisked positions in any preceding formula indicate relative stereochemistry. In other embodiments, stereochemical configurations depicted at asterisked positions indicate absolute stereochemistry. In certain particular embodiments, the invention relates to compounds of formula wherein the stereochemical configurations depicted at asterisked positions indicate absolute stereochemistry.

General Synthetic Methodology

Compounds of formula (II), (IIa), (III) and $R^{r'}$NHS(O)$_2$Cl can be prepared by methods known to one of ordinary skill in the art and/or by reference to the schemes shown below and the synthetic examples that follow. Exemplary synthetic routes are set forth in Schemes 1, 2 and 3 below, and in the Examples.

Scheme 1: General route for the synthesis of (1S,2S,4R)-4-amino-2-nydroxylmethyl)cyclopentanols

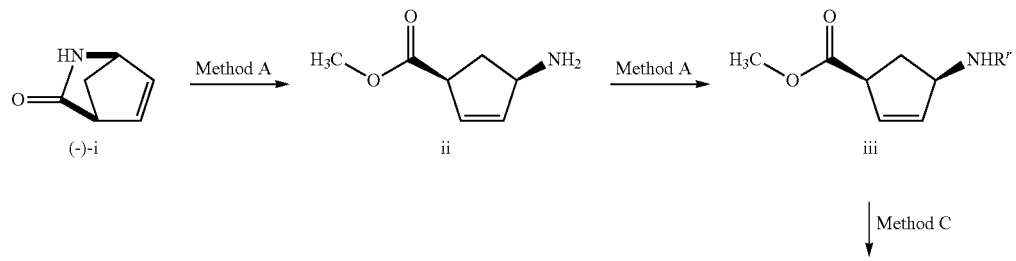

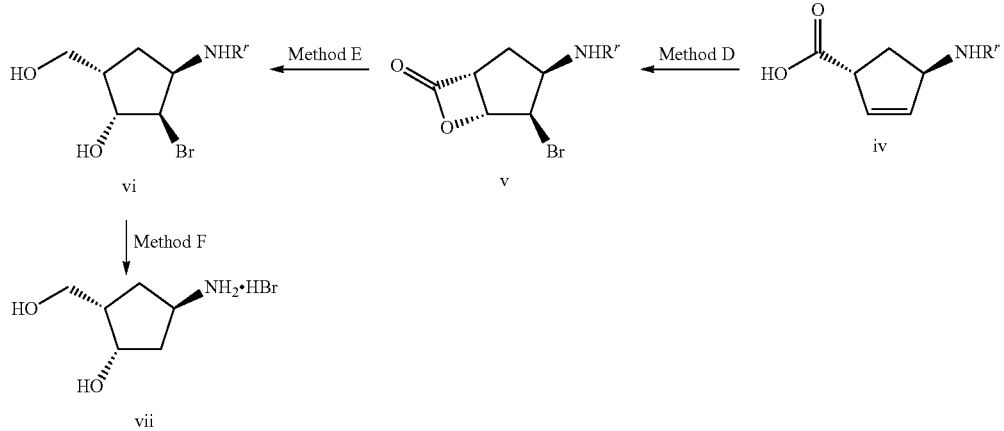

Scheme 1 and 2 show general routes for preparing compounds of formula (IIa), wherein each of $R^b$, $R^d$, $R^e$, $R^{e'}$, $R^h$, and $R^{h'}$ is hydrogen. Those of ordinary skill in the art will recognize that compounds of formula (IIa) wherein one or more of $R^b$, $R^d$, $R^e$, $R^{e'}$, $R^h$, and $R^{h'}$ is other than hydrogen can also be prepared by the same general route beginning with appropriate starting materials analogous to i.

Lactams such as (−)-i are commercially available, and conversion of compounds of formula i to those of formula iii is accomplished by methods such as those detailed in Scheme 1 (see Smith et al. *Tetrahedron. Lett.,* 2001, 42, 1347). Treatment of lactam i with thionyl chloride in methanol affords ii which is then protected with a suitable amino protecting group $R^r$ to give compounds of formula iii (Method A). Alternatively, protection of the amino group can occur first, followed by acid catalyzed ring-opening with a suitable acid such as hydrochloric acid in methanol to give compounds of formula iii (Method B; see Bray et al. *Tetrahedron Lett.,* 1995, 36, 4483). Compounds of formula iii also serve as the starting material in the alternate general synthesis of compounds of formula (IIa) detailed below in Scheme 2.

Base mediated hydrolysis of the ester in compounds of formula iii forms compounds of formula iv with epimerization. This transformation may be conducted using an appropriate base such as sodium hydroxide in appropriate solvents such as tetrahydrofuran and methanol (Method C). Bromination and lactonization to generate compounds of formula v (Method D) may be effected by treatment of compounds of formula iv with tetrabutylammonium hydroxide, followed by treatment with bromine in an appropriate solvent such as methylene chloride or tetrahydrofuran. Prior to the treatment with bromine the reaction mixture is cooled to an appropriate temperature in the range of about 0° C. to −70° C. The reaction mixture is kept below about 20° C. during the course of the reaction. Other reagents that can be used instead of tetrabutylammonium hydroxide, prior to the addition of bromine, include, but are not limited to, sodium hydrogen carbonate, potassium phosphate, pyridine, or mixtures thereof. Other suitable solvents for this transformation include, but are not limited to, ethyl acetate, methanol, water, dimethoxyethane, or mixtures thereof.

Reduction of the lactone in compounds of formula v with a reducing agent yields compounds of formula vi (Method E). Suitable reducing agents for this transformation include lithium tetrahydroborate. Appropriate solvents for this transformation include tetrahydrofuran, diethyl ether and the like. The solution of compounds of formula v is generally cooled, preferably in the range of about −20° C. to 0° C. prior to the addition of the reducing agent. A second reagent, such as, but not limited to, copper chloride, or palladium chloride may also be employed in addition to the lithium tetrahydroborate. Other suitable reagents for the transformation of compounds of formula v to those of formula vi include lithium aluminium hydride, diisobutylaluminium hydride, and sodium borohydride. Other suitable solvents for this transformation include isopropanol, methanol, and dimethylsulfoxide which may contain up to about 10% water. Other suitable temperatures ranges for this transformation are in the range of about 0° C. to about 40° C.

Removal of the protecting group $R^r$ and de-bromination in compounds of formula vi (Method F) then affords compound vii. These transformations can be accomplished in a number of ways known to one of ordinary skill in the art, depending on the protecting group $R^r$ that is used. In some embodiments, $R^r$ is a hydrogen-labile protecting group. In such embodiments deprotection and de-bromination are accomplished in a single step. This may include treatment with hydrogen gas in the presence of a palladium catalyst in an appropriate solvent such as methanol. This transformation yields compounds of formula vii as their hydrobromide salts. In other embodiments, removal of the protecting group $R^r$ and de-bromination may be accomplished in separate steps. In some embodiments the hydrochloride salts of compounds of formula vii can be generated.

When the protecting group $R^r$ is acid-labile, following its removal with HBr or HCl, the hydrobromide or hydrochloride salt of the compound of formula vi, where $R^r$ is H, is generated. This compound is then treated with hydrogen to accomplish de-bromination and yield the compound of formula vii. The debromination can be accomplished using a suitable palladium catalyst, a suitable base and a suitable solvent. Suitable catalysts include Pd/C. Suitable bases include, but are not limited to, triethylamine, N,N'-diisopropylethylamine, pyridine, tetrabutylammonium hydroxide and sodium hydrogen carbonate. Suitable solvents include, but are not limited to, isopropyl alcohol and methanol.

Scheme 2: Alternate general route fot the synthesis of (1S,2S,4R)-4-amino-2-nydroxylmethyl)cyclopentanols

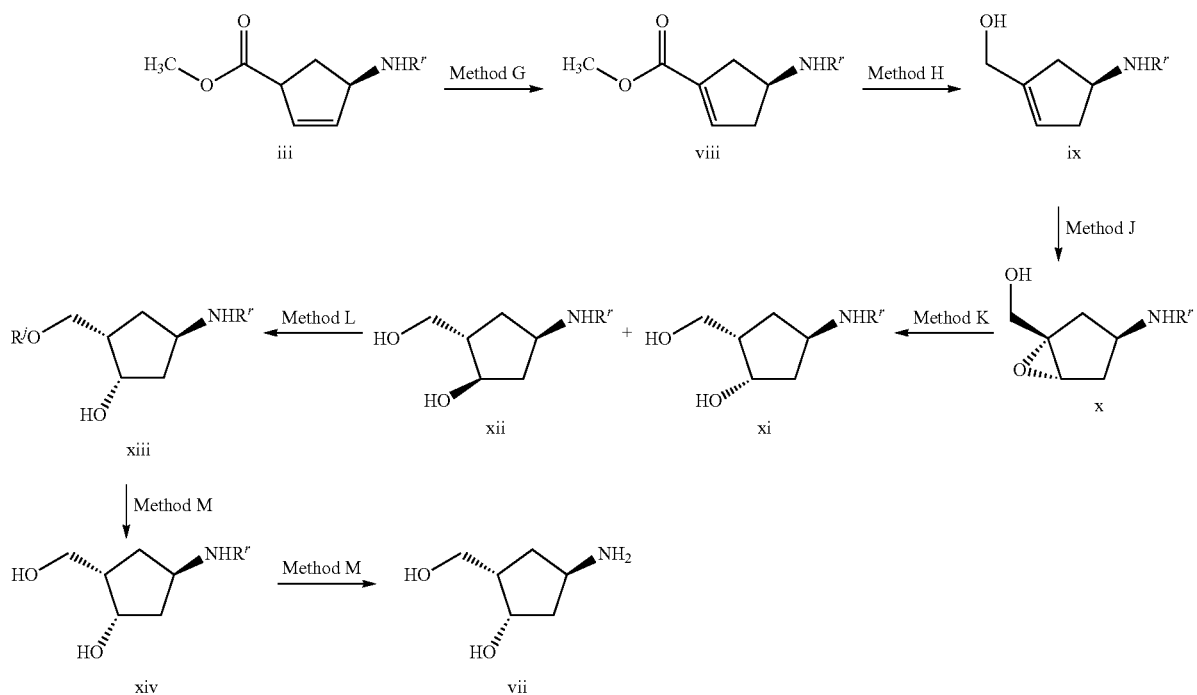

Scheme 2 details an alternate general route for the synthesis of compounds of general formula (IIa) wherein each of $R^b$, $R^d$, $R^e$, $R^{e'}$, $R^h$, and $R^{h'}$ is hydrogen. The starting material iii can be prepared as detailed in Scheme 1 above. Conversion of compounds of formula iii to compounds of formula viii can be accomplished by treatment with diazabicyclo[5.4.0]undec-7-ene (Method G) in an appropriate solvent such as methylene chloride (see Bray et al. *Tetrahedron Lett.*, 1995, 36, 4483).

Reduction of the ester group in compounds of formula viii to give compounds of formula ix is accomplished by treatment with a suitable reducing agent such as diisobutylaluminium hydride or the like in an appropriate solvent such as toluene or tetrahydrofuran (Method H). The solution of compounds of formula viii is generally cooled, preferably in the range of about −20° C. to about 0° C. prior to the addition of the reducing agent.

Epoxidation of the double bond in compounds of formula ix to generate compound of formula x is achieved by known methods (Method J) (see Gao et al. *J. Am. Chem. Soc.*, 1987, 5765). A solution of the compound of formula ix is added slowly to a cooled mixture of (+)-diethyl-L-tartrate and titanium (IV) isopropoxide in methylene chloride. The rate of addition of compounds of formula ix is such that the reaction temperature is maintained in range of about −25° C. to about −45° C. To this, tert-butyl hydroperoxide is added slowly such that the reaction temperature is maintained in range of about −25° C. to about −45° C.

Regiospecific ring opening of the epoxide in compounds of formula x to afford compounds of formula xi can be accomplished by treatment of a solution of the compound of formula x with sodium borohydride and borane-THF complex (see Brown and Yoon *J. Am. Chem. Soc.*, 1968, 90, 2686) in an appropriate solvent such as methylene chloride (Method K).

The reaction to generate compounds of formula xi may also generate amounts of compounds of formula xii as a minor product. The primary alcohol in compounds of formula xi may be selectively protected with a bulky protecting group ($R^j$) such as triisopropylsilyl or tert-butyldiphenylsilyl to afford compounds of formula xiii which can be separated from compounds of formula xii by purification methods known to one of ordinary skill in the art, such as column chromatography. The introduction of the silyl protecting group may be effected by known methods such as treatment with the appropriate silyl chloride in the presence of a base such as triethylamine or N,N'-diisopropylethylamine in a solvent such as methylene chloride (Method L).

Following purification, the silyl protecting group may be selectively removed from compounds of formula xiii to give compounds of formula xiv. This transformation may be accomplished by treatment of a cooled solution of a compound of formula xiii with a solution of tetrabutylammonium fluoride (TBAF) in an appropriate solvent such as tetrahydrofuran (Method M).

Removal of the protecting group $R^r$ affords compounds of formula vii (Method F). This transformation can be accomplished in a number of ways known to one of ordinary skill in the art depending on the protecting group $R^r$ that is used. For example, in some embodiments, the protecting group $R^r$ is subject to hydrogenolysis, and deprotection can be effected by treatment with hydrogen gas in the presence of a palladium catalyst (Method F) in an appropriate solvent such as methanol. In some other embodiments, the protecting group $R^r$ is acid-labile and deprotection can be effected by an acid.

Either or both of the hydroxyl groups in compounds of formula vi, vii or xiv in Schemes 1 or 2 may be protected with a hydroxyl protecting group or a cyclic diol protecting group using methods known to one of ordinary skill in the art.

Compounds of formula (III) may be prepared according to methods such as that described by J. A. Montgomery and K. Hewson, *J. Med. Chem.*, 1967, 10, 665.

Scheme 3: General route for the synthesis of substituted-(chlorosulfonyl)carbamates R"NHS(O)₂Cl

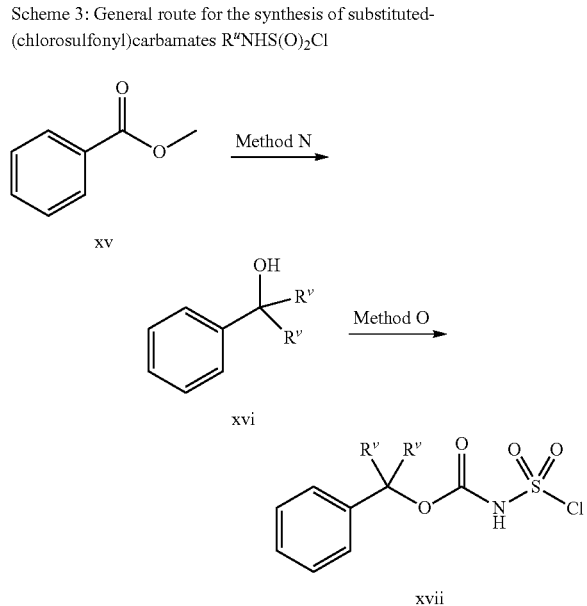

Scheme 3 shows a general routes for preparing compounds of formula R"NHS(O)₂Cl wherein R" is —C(O)OC(R')₂(R") and R" is phenyl. Those of ordinary skill in the art will recognize that compounds of formula R"NHS(O)₂Cl wherein R" is other than phenyl can also be prepared by the same general route beginning with appropriate starting materials analogous to xv.

Starting from a commercially available methylbenzoate xv, treatment with a Grignard reagent R'MgCl in an appropriate solvent such as tetrahydrofuran affords compounds of formula xvi (Method N). The solution of the compounds of formula xv is cooled to about 0° C. prior to the addition of the Grignard reagent which is added at a rate sufficient to keep the temperature of the reaction mixture below about 10° C. A solution of xvi is then added to a cooled solution of chlorosulfonyl isocyanate in an appropriate solvent such as tetrahydrofuran to afford compounds of formula xvii. The addition of the solution of compounds of formula xvi is at a rate sufficient to keep the temperature of the reaction mixture below about 10° C. (Method O). The resulting substituted-(chlorosulfonyl)carbamate reagent xvii is then stored with as a solution in an appropriate solvent such as tetrahydrofuran until use.

The compound of formula R"NHS(O)₂Cl wherein R" is —C(O)OC(CH₃)₃, may be prepared according to methods such as that described in Hirayama et al. *Bioorg. Med. Chem.*, 2002, 10, 1509-1523. The compound of formula R"NHS(O)₂Cl wherein R" is —C(O)N(Ph)₂ may be prepared in a manner similar to that described in U.S. Pat. Appl. Publ. (2005), US 2005282797 A1.

The amines used in Example 18 can be made by methods disclosed in Langston S. et al. U.S. patent application Ser. No. 11/700,614, which is hereby incorporated by reference in its entirety.

In order that this invention be more fully understood, the following preparative and testing examples are set forth.

These examples illustrate how to make or test specific compounds, and are not to be construed as limiting the scope of the invention in any way.

EXAMPLES

ABBREVIATIONS

AcOH acetic acid
BINAP 2,2'-bis(diphenylphosphino)-1,1'-binaphthyl
Boc tert-butoxycarbonyl
DCM methylene chloride
DI deionized
DMAP 4-dimethylaminopyridine
DMF dimethylformamide
DMF-DMA dimethylformamide dimethylacetal
DMSO dimethylsulfoxide
EtOAc ethyl acetate
EtOH ethanol
iPrOAc isopropyl acetate
MCPBA meta-chloroperbenzoic acid
MeOH methanol
MTBE methyl tert-butyl ether
THF tetrahydrofuran
h hours
HRMS high resolution mass spectrum
min minutes
m/z mass to charge
MS mass spectrum
RP LC-MS reverse phase liquid chromatography-mass spectrometry
TLC thin-layer chromatography Proton nuclear magnetic resonance spectra were obtained on a Varian Mercury 300 spectrometer at 300 MHz, on a Bruker AVANCE 300 spectrometer at 300 MHz, or on a Bruker AVANCE 500 spectrometer at 500 MHz.

LCMS conditions: spectra were run on a Phenomenex Luna 5µ C18(2) 150×4.6 mm column on an Agilent 1100 series instrument at 1 ml/min for a 20 minute run using the following gradients:

Method Formic Acid (FA): Mobile phase A consisting of 99% v/v water, 1% v/v acetonitrile, 0.1% v/v formic acid. Mobile phase B consisting of 95% v/v acetonitrile, 5% v/v water, 0.1% v/v formic acid. Method follows a gradient of 5% B to 100% B over 12 minutes, maintaining at 100% B for 3 minutes and returning to 5% B over 1 minute and maintaining until end of method.

Method Ammonium Acetate (AA): Mobile phase A consisting of 100% water (with 10 mM ammonium acetate, pH=4.5). Mobile phase B consisting of 95% v/v acetonitrile, 5% v/v water (with 10 mM ammonium acetate, pH=4.5). Method follows a gradient of 5% B to 100% B over 12 minutes, maintaining at 100% B for 3 minutes and returning to 5% B over 1 minute and maintaining 5% B until end of run.

Thin-layer chromatography (TLC) was performed using EMD silica-gel 60 plates and visualized by ultraviolet (UV) light.

HPLC analyses were run on a Phenomenex Luna 5µ C18(2) 150×4.6 mm column on an Agilent 1100 series instrument at 1.0 ml/min for a 30 minute run using the following gradients:

Method Ammonium Acetate (AA2): Mobile phase A consisting of 100% water (with 10 mM ammonium acetate, pH=4.5). Mobile phase B consisting of 95% v/v acetonitrile, 5% v/v water (with 10 mM ammonium acetate, pH=4.5). Method follows a gradient of 30% B to 70% B over 12 minutes, form 70% B to 100% B over 5 minutes maintaining at 100% B for 3 minutes and returning to 30% B over 5 minutes and maintaining 30% B until end of run.

Example 1: Methyl-(1S,4R)-4-aminocyclopent-2-ene-1-carboxylate Hydrochloride (−)-2-Azabicyclo[2,2,1]hept-5-en-3-one (20.00 g, 0.1833 mmol) was dissolved in MeOH (140 mL) and this mixture was cooled to 0° C. Thionyl chloride (29.4 mL, 0.403 mol) was then added dropwise, keeping the temperature less than 15° C. Upon completion of addition, the mixture was left to stir at 5° C. for 2 hours. The solvent was removed under reduced pressure to yield an oil, which was dried further under high vacuum overnight at 35° C. to afford the title compound as a white solid (33 g) which was used without further purification. $^1$H NMR (300 MHz, DMSO, δ): 8.45 (s, 3H), 6.03 (m, 1H), 5.87 (m, 1H), 4.13 (m, 1H), 3.60 (m, 4H), 2.53 (m, 1H) and 1.89 (m, 1H).

Example 2: Methyl (1S,4R)-4-(tritylamino)cyclopent-2-ene-1-carboxylate

Methyl-(1S,4R)-4-aminocyclopent-2-ene-1-carboxylate hydrochloride (5.50 g) was suspended in methylene chloride (60 mL), to which triphenylmethyl chloride (9.06 g, 0.0325 mol) was added. The mixture was then cooled to 0° C. Triethylamine (10.8 mL, 0.0774 mol) was then added dropwise keeping the temperature less than 10° C. Upon completion of addition, the mixture was allowed to warm to 20-25° C. The mixture was left to stir at 20-25° C. for 17 hours. The mixture was then washed with water (3×50 mL). The aqueous washes were combined and extracted with DCM (50 mL). The organics were combined and washed with brine (20 mL) and the solvent was removed under reduced pressure to afford the title compound as a brown oil (12.5 g) which was used without further purification. $^1$H NMR (300 MHz, CDCl$_3$, δ): 7.58 (m, 6H), 7.27 (m, 6H), 7.18 (m, 3H), 5.57 (m, 1H), 4.93 (m, 1H), 3.76 (m, 1H), 3.65 (s, 3H), 3.18 (m, 1H), 2.11 (m, 1H), 1.90 (m, 1H) and 1.53 (m, 1H).

Example 3: (1R,4R)-4-(tritylamino)cyclopent-2-ene-1-carboxylic Acid

Methyl (1S,4R)-4-(tritylamino)cyclopent-2-ene-1-carboxylate (11.00 g, 0.02868 mol) was dissolved in tetrahydrofuran (50 mL) and methanol (50 mL). Sodium hydroxide (2.06 g, 0.0516 mol) in water (60 mL) was added and the mixture stirred at ambient temperature for 18 hours. TLC (20% EtOAc/Hexane) showed no starting material. 20% w/v citric acid in water was added dropwise at ambient temperature until the mixture was pH 6. The mixture was then extracted with methylene chloride (3×100 mL). The organic layers were combined and dried over Na$_2$SO$_4$, filtered and concentrated to give a white foam (10 g). TLC (50% EtOAc/Hexane) shows 2 diastereomers. The mixture was purified using column chromatography, eluting with 50% EtOAc/Hexane to afford the title compound (1.3 g) as a white solid. $^1$H NMR (300 MHz, DMSO, δ): 7.47 (m, 6H), 7.30 (m, 6H), 7.17 (m, 3H), 5.49 (m, 1H), 4.88 (m, 1H), 3.70 (m, 1H), 3.35 (m, 1H), 1.84 (m, 1H) and 1.43 (m, 1H). LCMS: R$_f$=12.95 mins, ES$^+$=370 (AA).

Example 4: (1R,3R,4R,5R)-4-bromo-3-(tritylamino)-6-oxabicyclo[3.2.0]heptan-7-one To (1R,4R)-4-(tritylamino)cyclopent-2-ene-1-carboxylic acid (0.9 g, 0.0024360 mol) dissolved in methylene chloride (20 mL), was added 31% tetrabutylammonium hydroxide in MeOH (2.579 mL), and the mixture was stirred for 30 minutes at ambient temperature. The mixture was concentrated under reduced pressure. The resultant residue was then dissolved in methylene chloride (20 mL, 0.3 mol) and cooled to −70° C. under a blanket of N$_2$. Bromine (251 uL, 0.00487 mol) in 5 ml of methylene chloride was then added dropwise and the mixture was stirred at −70° C. for 1 hour, then warmed to 0° C. Upon reaching 0° C., 20 mL of 5% w/v Na$_2$SO$_3$ in water was added dropwise and mixture was allowed to warm to ambient temperature. The reaction mixture was extracted with methylene chloride (3×10 mL), organic layers were combined and dried over Na$_2$SO$_4$, filtered and concentrated to give a red residue. The residue was filtered through a silica gel plug, eluting with 0 to 30% EtOAc/Hexane to remove inorganics and impurities to afford the title compound (0.73 g) as a white solid. $^1$H NMR (300 MHz, DMSO, δ): 7.49 (m, 6H), 7.24 (m, 9H), 4.95 (d, 1H), 3.91 (m, 1H), 3.65 (m, 1H), 2.97 (m, 1H), 2.66 (m, 1H), 1.62 (m, 1H) and 1.20 (m, 1H). LCMS: R$_f$=14.40 mins, ES$^+$Na=470 (AA).

Example 5: (1R,2R,3R,5S)-2-bromo-5-(hydroxymethyl)-3-(tritylamino)cyclopentanol (1R,3R,4R,5R)-4-bromo-3-(tritylamino)-6-oxabicyclo [3.2.0]heptan-7-one (0.6 g, 0.0013382 mol) was dissolved in diethyl ether (20 mL) and the mixture was cooled to 0° C. Lithium tetrahydroborate (0.087 g, 0.004015 mol) was added in one portion and the mixture was stirred at 0° C. for 1 hour, then allowed to warm to ambient temperature and stirred for a further 1 hour. TLC (20% EtOAc/Hexane) showed no starting material. The reaction mixture was cooled to 0° C. at which point saturated NH$_4$Cl aq (20 mL) was added dropwise maintaining a temperature less than 5° C. The mixture was allowed to warm to ambient temperature and extracted with methylene chloride (3×20 mL). The organics were combined and dried over Na$_2$SO$_4$, filtered and concentrated to afford the title compound (0.61 g) as a white solid which was used without further purification. $^1$H NMR (300 MHz, CD$_3$OD, δ): 7.56 (m, 6H), 7.25 (m, 9H), 4.15 (m, 1H), 3.55 (m, 1H), 3.40 (m, 2H), 2.90 (m, 1H), 2.53 (m, 1H) and 1.63 (m, 2H). LCMS: R$_f$=13.30 mins, ES$^+$Na=474 (AA).

Example 6: (1S,2S,4R)-4-amino-2-(hydroxymethyl)cyclopentanol.HBr (1R,2R,3R,5S)-2-bromo-5-(hydroxymethyl)-3-(tritylamino)cyclopentanol (0.4 g, 0.0008842 mol) was dissolved in MeOH (10.0 mL). To this mixture was added 5% palladium on charcoal, (0.28 g). The resulting mixture was stirred under a balloon of hydrogen (1000 mL, 0.04 mol) for 18 hours at 40° C. An aliquot was syringe filtered and concentrated. $^1$H NMR indicated that the reaction had gone to completion so the entire reaction mixture was filtered through a pad of celite and the filtrate concentrated. This sticky solid was triturated with 5 mL of THF, filtered and the bed washed with tert-butylmethyl ether. The resulting solid was dried under vacuum at ambient temp to afford the title compound (0.125 g) as a white solid which was used without further purification. $^1$H NMR (300 MHz, CD$_3$OD, δ): 4.38 (t, J=4.08 Hz, 1H), 3.82 (m, 1H), 3.72 (m, 1H), 3.60 (m, 1H), 2.31 (m, 1H), 2.22 (m, 1H), 2.03 (m, 1H) and 1.78 (m, 2H).

Example 7: Methyl (4S)-4-(tritylamino)cyclopent-1-ene-1-carboxylate

A reactor was charged with a solution of methyl (1S,4R)-4-(tritylamino)cyclopent-2-ene-1-carboxylate (4.75 kg, 12.4 mol) in methylene chloride. The reactor was charged with additional methylene chloride (15 L) to bring the total volume to 23.8 L. To the stirred solution was added 1,8-diazabicyclo[5.4.0]undec-7-ene (4.82 L, 32.2 mol). The reaction mixture was warmed to 40° C., with stirring for 16 to 22 h. $^1$H NMR (CDCl$_3$) analysis of a small sample of the reaction mixture confirmed the formation of the product. The reaction was washed with 10% aqueous citric acid solution (2×7 L). The organic phase was concentrated under reduced pressure to afford the title compound as an oil. The oil was diluted with anhydrous toluene and concentrated to remove residual water and used without further purification. $^1$H NMR (300 MHz, CDCl$_3$, δ): 7.60-7.54 (m, 5H), 7.34-7.17 (m, 10H), 6.53-6.50 (m, 1H), 3.70 (s, 3H), 3.50-3.40 (m, 1H), 2.60-2.52 (dd, J=16.6, 8.3 Hz, 1H), 2.24-2.20 (m, 1H), 2.16-2.05 (m, 1H) and 1.91-1.80 (m, 1H).

Example 8: [(4S)-4-(tritylamino)cyclopent-1-en-1-yl]methanol

A reactor was charged with methyl (4S)-4-(tritylamino) cyclopent-1-ene-1-carboxylate (4.75 kg, 12.4 mol). The reactor was charged with anhydrous toluene (9.5 L), cooled to −5 to −10° C. and the agitation started. While maintaining the temperature between −10° C. and +10° C., diisobutyl-aluminum hydride (1M solution in toluene, 23.4 kg, 27.3 mol) was added. Upon completion of the addition, the reaction mixture was analyzed by HPLC, which confirmed a complete conversion of the starting material to the product. The reaction mixture was quenched into cold 2 N NaOH solution (−5 to −10° C.) at a rate to keep the internal temperature below 20° C. The organic phase was separated and filtered through a pad of diatomaceous earth. The pad was washed with toluene (2×1 L), and the filtrate was concentrated under reduced pressure to afford the title compound as a thick oil (5.15 kg). The product was diluted with methylene chloride and stored as a solution at 0 to 5° C. $^1$H NMR (300 MHz, CDCl$_3$, δ): 7.60-7.56 (m, 5H), 7.35-7.17 (m, 10H), 5.38 (bs, 1H), 4.03-4.02 (d, J=3.7 Hz, 2H), 3.49-3.36 (m, 1H), 2.40 (s, 2H), 2.19-1.79 (m, 4H), 1.32-1.29 (t, J=5.8 Hz, 1H).

Example 9: [(1S,3S,5S)-3-(tritylamino)-6-oxabicyclo[3.1.0]hex-1-yl]methanol

A reactor was charged with (+)-diethyl-L-tartrate (2.23 L, 13.0 mol) and methylene chloride (10.5 L). Stirring was started and the mixture was cooled to −30 to −40° C. Titanium (IV) isopropoxide (3.93 L, 13.4 mol) was slowly added while maintaining the internal temperature between −30 to −40° C. A solution of [(4S)-4-(tritylamino)cyclopent-1-en-1-yl]methanol (4.2 kg, 11.8 mol) in methylene chloride (19 L) was slowly added to the reaction mixture, while maintaining the temperature between −30 to −40° C. After stirring for 20 minutes, t-butyl hydroperoxide (5-6 M in decane, 3.3 L, 16.3 mol) was slowly added while maintaining the temperature between −30 to −40° C. Upon completion of the addition, the reaction mixture was analyzed by HPLC, which confirmed the formation of the product and presence of 3% (AUC) of the starting material. The reaction mixture was carefully quenched into a 100-L reactor containing a cold aqueous solution (0 to 5° C.) of iron (II) sulfate heptahydrate (10.5 kg) and tartaric acid (6.3 kg) in DI water (42 L). After stirring for 15 minutes, the organic phase was separated and filtered through a pad of diatomaceous earth. The pad was washed with methylene chloride (2×2 L), and the filtrate was transferred into a 100-L reactor. A cold solution (0 to 5° C.) of solid sodium hydroxide (3.36 kg) in brine (42 L) was slowly added to the gently stirred reaction mixture. After 1 h, the organic phase was separated, dried over anhydrous sodium sulfate, filtered through a pad of diatomaceous earth and concentrated under reduced pressure to give a brown oil. This was purified via silica-gel chromatography using five columns. Each column was performed as follows. A 20 cm diameter glass column was loaded with a slurry of silica gel (5 kg) in 30% ethyl acetate/heptane with 0.5% triethylamine added. Crude product (~1.2 kg) was adsorbed onto silica gel (1.5 kg) and loaded on the column. Polarity was gradually increased from 30% to 40% ethyl acetate/heptane with 0.5% triethylamine. Combined purified material from all columns afforded the title compound (3.93 kg, 89% yield) as an amber oil. $^1$H NMR (300 MHz, CDCl$_3$, δ) 7.54-7.50 (m, 5H), 7.32-7.18 (m, 10H), 3.80-3.76 (d, J=12.5 Hz, 1H), 3.65-3.61 (d, J=12.5 Hz, 1H), 3.31 (s, 1H), 3.03-2.92 (m, 1H), 1.77-1.69 (m, 2H) and 1.37-1.13 (m, 2H).

Example 10: (1S,2S,4R)-2-(hydroxymethyl)-4-(tritylamino)cyclopentanol and (1S,3S)-1-(hydroxymethyl)-3-(tritylamino)cyclopentanol A reactor was charged with a methylene chloride solution of [(1S,3S,5S)-3-(tritylamino)-6-oxabicyclo[3.1.0]hex-1-yl] methanol (2.76 kg, 7.4 mol). The reactor was charged with additional methylene chloride (5 L) to bring the total to 13.8 L. The stirred reaction mixture was heated to 35° C. to 40° C. Using a solid addition system, sodium borohydride (281 g, 7.4 mol) was added portion wise while maintaining the temperature between 35° C. and 45° C. Borane-THF complex (1 M solution in THF, 6.7 kg, 7.4 mol) was slowly added while maintaining the temperature between 35 to 45° C. The temperature was maintained at 35 to 40° C. for 1 hour, and then the reaction mixture was analyzed by HPLC. The reaction was deemed complete when the amount of starting material was less than 2%. The reaction mixture was cooled to less than 30° C., then carefully quenched into a 100-L reactor containing cold DI water (28 L). After stirring for 3 hours, the organic phase was separated and dried over anhydrous magnesium sulfate, filtered through a pad of diatomaceous earth and concentrated under reduced pressure to afford a mixture of (1S,2S,4R)-2-(hydroxymethyl)-4-(tritylamino)cyclopentanol and (1S,3S)-1-(hydroxymethyl)-3-(tritylamino)cyclopentanol (2.74 kg) as a brown oil, which was used without further purification.

Example 11: (1S,2S,4R)-2-{[(triisopropylsilyl)oxy] methyl}-4-(tritylamino)cyclopentanol A reactor was charged with the mixture of (1S,2S,4R)-2-(hydroxymethyl)-4-(tritylamino)cyclopentanol and (1S,3S)-1-(hydroxymethyl)-3-(tritylamino)cyclopentanol (1.87 kg total, ~280 g of (1S,2S,4R)-2-(hydroxymethyl)-4-(tritylamino)cyclopentanol, 0.75 mol). The reactor was charged with methylene chloride (7.4 L) and the agitation started. While maintaining the temperature less than 25° C., triethylamine (210 mL, 1.5 mol) was added. While maintaining the temperature less than 25° C., triisopropylsilyl chloride (402 mL, 1.9 mol) was slowly added. The reaction mixture was allowed to stir at 20° C. to 22° C., for ~48 hours. The reaction mixture was analyzed by TLC (50% ethyl acetate/heptane, UV visualization), which indicated the formation of the product (R$_f$ 0.70) and the presence of unreacted (1S,3S)-1-(hydroxymethyl)-3-(tritylamino)cyclopentanol (R$_f$ 0.15). The clear pale yellow solution was cooled to 5 to 10° C., slowly quenched with DI water (7.5 L), and the resulting layers separated. The aqueous phase was extracted with methylene chloride (3 L) and the combined organic phases were dried over anhydrous magnesium sulfate, filtered through a pad of diatomaceous earth and concentrated under reduced pressure to give a brown oil (4.06 kg), which was purified by silica gel chromatography using multiple columns. Each column was performed as follows. A 20 cm diameter glass column was loaded with a slurry of silica gel (4.5 kg) in 10% ethyl acetate/heptane. The oil (~1.2 kg) was loaded on the column. Combined purified material from all columns afforded the title compound (2.94 kg) as a clear oil which was used without further purification. $^1$H NMR (300 MHz, CDCl$_3$, δ): 7.56-7.54 (m, 5H), 7.34-7.13 (m, 10H), 4.26 (bs, 1H), 3.86-3.81 (dd, J=10.0, 4.5 Hz, 1H), 3.65-3.60 (dd, J=10.1, 7.2 Hz, 1H), 3.41-3.37 (m, 1H), 3.07 (bs, 1H), 2.16-2.07 (m, 1H), 1.69-1.63 (m, 3H), 1.47-1.20 (m, 4H) and 1.08-1.03 (2 s, 18H).

Example 12: (1S,2S,4R)-2-(hydroxymethyl)-4-(tritylamino)cyclopentanol

A reactor was charged with (1S,2S,4R)-2-{[(triisopropylsilyl)oxy]methyl}-4-(tritylamino)cyclopentanol (2.94 kg total, ~1.6 kg assumed pure material, 3.02 mol,). The reactor was charged with THF (6 L) and agitation started. While maintaining the temperature less than 25° C., tetrabutylammonium fluoride (1M solution in THF, 3.02 L, 3.0 mol) was added. The reaction mixture was allowed to stir at 20° C. to 22° C., for 3 hours. TLC (50% ethyl acetate/heptane, UV visualization) confirmed a complete conversion of the starting material to the product. The reaction mixture was concentrated under reduced pressure to ~2 L volume and transferred to a second reactor. The concentrate was diluted with methylene chloride (16 L), washed with saturated aqueous ammonium chloride (8 L), and DI water (8 L). The organic phase was dried over anhydrous magnesium sulfate, filtered through a pad of diatomaceous earth and concentrated under reduced pressure to give an amber oil (3.88 kg) which was purified by silica gel chromatography. Two columns were performed as follows. A 20 cm diameter glass column was loaded with a slurry of silica gel (5 kg) in 10% ethyl acetate/heptane. About 1.9 kg of the oil was adsorbed onto silica gel (1.5 kg) and loaded on the column and the polarity was gradually increased from 10% to 50% ethyl acetate/heptane. Pure fractions were combined and concentrated under reduced pressure to afford the title compound (800 g) as a white solid. $^1$H NMR (300 MHz, CDCl$_3$, δ): 7.57-7.53 (m, 5H), 7.32-7.18 (m, 10H), 4.26-4.23 (m, 1H), 3.65-3.46 (m, 2H), 3.36-3.29 (m, 1H), 2.17-2.07 (m, 2H), 1.65-1.62 (d, 1H), 1.51-1.39 (m, 2H), 1.37-1.26 (m, 1H) and 1.2-1.17-1.11 (m, 1H).

Example 13: (1S,2S,4R)-4-amino-2-(hydroxymethyl)cyclopentanol

A hydrogenation reactor was purged with argon and charged with 5% palladium on carbon (50% water wet, 80 g, 20 mol %) and the reactor sealed. Using vacuum, a solution of (1S,2S,4R)-2-(hydroxymethyl)-4-(tritylamino) cyclopentanol (400 g, 1.07 mol) in methanol (2.7 L) was added to the reactor. The reactor was purged with argon, charged to 35 to 45 psi hydrogen and heated to 35° C. for 72 h. The reaction mixture was filtered through a pad of diatomaceous earth, washed with methanol (32 L) and concentrated under reduced pressure to ~1 L volume. Precipitated triphenyl methane was filtered from the mixture and the filtrate further concentrated to give an amber oil. The crude material was purified by silica-gel chromatography. The column was performed as follows. A 15 cm diameter glass column was loaded with a slurry of silica gel (1.6 kg) in methylene chloride. The amber oil was adsorbed onto silica gel (200 g) and loaded on the column. The polarity was gradually increased from 100% methylene chloride to 50% methylene chloride/methanol. The pure fractions were combined and concentrated under reduced pressure to afford the title compound (118 g) as a waxy yellow solid. $^1$H NMR (300 MHz, CD$_3$OD, δ): 4.35-4.32 (m, 1H), 3.76-3.70 (m, 1H), 3.64-3.56 (m, 2H), 2.34-2.26 (m, 1H), 2.10-2.03 (m, 1H), 1.93-1.82 (m, 1H) and 1.63-1.46 (m, 2H).

Example 14: (1S,2S,4R)-4-(4-chloro-7H-pyrrolo[2,3-d]pyrimidin-7-yl)-2-(hydroxymethyl)cyclopentanol To a slurry of 4,6-dichloro-5-(2,2-diethoxyethyl)pyrimidine (10.0 g, 0.0377 mol) and (1S,2S,4R)-4-amino-2-(hydroxymethyl)cyclopentanol.HBr (8.00 g) in isopropyl alcohol (82 mL, 1.1 mol) and water (11 mL, 0.59 mol), triethylamine (13 mL, 0.094 mol) was added. This mixture was then heated to 85° C. for 23 hours. The mixture was cooled to 50° C., at which point 4M hydrochloric acid in water (20 mL) was added slowly. The resulting mixture was then stirred at 50° C. for 3 hours. HPLC indicated that the reaction was complete. The reaction mixture was cooled to ambient temperature and sodium bicarbonate (10 g, 0.1 mol) was added portionwise. Excess solids were filtered; the bed washed with isopropyl alcohol (20 mL) and the filtrate concentrated to ~70 mL. Ethyl acetate (150 mL) was added followed by a mixture of saturated NaHCO$_3$ aq (35 mL) and water (35 mL). The layers were separated and the aqueous phases extracted with ethyl acetate (2×50 mL) and filtered. The organic layers were combined and washed with saturated NaCl aq (50 mL) and then concentrated to afford the title compound (9.3 g) as a brown solid. $^1$H NMR (300 MHz, CD$_3$OD, δ): 8.56 (s, 1H), 7.67 (d, 1H), 6.65 (d, 1H), 5.52 (m, 1H), 4.50 (m, 1H), 3.79 (m, 1H), 3.66 (m, 1H), 2.63 (m, 1H), 2.25 (m, 3H) and 2.02 (m, 1H).

Example 15: (1S,2S,4R)-4-(4-chloro-7H-pyrrolo[2,3-d]pyrimidin-7-yl)-2-(hydroxymethyl)cyclopentanol A solution of (1S,2S,4R)-4-amino-2-(hydroxymethyl)cyclopentanol (250 mg, 1.90 mmol) and triethylamine (380 mg, 3.80 mmol) in 2-propanol (30 mL) was treated with 2-(4,6-dichloropyrimidin-5-yl)acetaldehyde (330 mg, 1.71 mmol) at 80° C. The reaction was monitored by HPLC and all aldehyde was found to have been consumed after 19 h. The reaction mixture was cooled to ambient temperature. Approximately 80% of the solvent was removed under reduced pressure and the resulting brown solution was added with stirring to water (30 mL). The resulting clear solution was cooled in an ice-water bath resulting in product crystallization. The resulting slurry was stirred at less than 5° C. for thirty minutes and filtered. The filter cake was washed with cold water (10 mL) and dried in a vacuum oven at 40° C. for 14 h to obtain the title compound as a brown solid (311 mg, 68% yield). $^1$H NMR (500 MHz, CDCl$_3$) δ 8.54 (s, 1H), 7.68 (d, J=3.7 Hz, 1H), 6.66 (d, J=3.6 Hz, 1H), 5.54 (m, 1H), 4.52 (m, 1H), 3.82 (dd, J=10.7, 7.2 Hz, 1H), 3.68 (dd, J=10.8, 6.5 Hz, 1H), 2.64 (m, 1H), 2.32 (m, 2H), 2.24 (m, 1H), 2.05 (m, 1H).

Example 16: 9-phenylheptadecan-9-ol

Methyl benzoate (14.34 g, 105.3 mmol) was dissolved in anhydrous THF (43 mL) and this mixture was cooled to 0° C. A solution of n-octylmagnesiumchloride in THF (200.0 mL, 2.0M, 400 mmol) was then added dropwise, keeping the temperature at less than 10° C. Upon completion of addition, the mixture was left to stir at 0° C. for 2 hours. A solution of hydrochloric acid in water (400 mL, 1.0 M) was then added dropwise keeping the temperature at less than 25° C. The mixture was diluted with iPrOAc (420 mL) and the resulting organic layer was washed with 1.0 M HCl (1×70 mL), washed with brine (1×70 mL), dried over sodium sulfate and evaporated to yield a colorless liquid. The crude material was purified by silica gel column chromatography to afford a clear colorless liquid (21.0 g). $^1$H NMR (300 MHz, CDCl$_3$, δ): 7.41-7.30 (m, 4H), 7.28-7.20 (m, 1H), 1.90-1.70 (m, 4H), 1.35-1.20 (m, 23H), 1.11-0.96 (m, 2H) and 0.92-0.83 (m, 6H).

Example 17: 1-octyl-1-phenylnonyl (chlorosulfonyl)carbamate

Chlorosulfonyl isocyanate (1.30 mL, 14.95 mmol) was dissolved in anhydrous THF (10 mL) and this mixture was cooled to 0° C. A solution of 9-phenylheptadecan-9-ol (4.972 g, 14.95 mmol) in anhydrous THF (18.5 mL) was added dropwise keeping the temperature at less than 10° C. Upon completion of addition, the mixture was left to stir at 0° C. for 1 hour. The resulting approximately 0.5 M solution of 1-octyl-1-phenylnonyl (chlorosulfonyl)carbamate was stored at 0° C. until use.

Example 18: General preparation of 4-amino substituted (1S,2S,4R)-(7H-pyrrolo[2,3-d]pyrimidin-7-yl)-2-(hydroxymethyl)cyclopentanols (1S,2S,4R)-4-(4-chloro-7H-pyrrolo[2,3-d]pyrimidin-7-yl)-2-(hydroxymethyl)cyclopentanol (1 equiv.), an amine as listed in Table 1 below (1.1 equiv.) and N,N'-diisopropylethylamine (1.3 equiv.) are mixed in 2-butanol (approximately 6 volumes). The reaction vessel is purged with nitrogen and then is heated under pressure (80 psi) at 135° C. for about 40 hours or until HPLC indicates little or no remaining starting material. The mixture is cooled to ambient temperature and pressure. Ethyl acetate is added to the reaction mixture and the organic layer is separated and washed with water. The aqueous layer is separated and washed with ethyl acetate. The combined organic layers are washed with saturated NaCl solution and dried over Na$_2$SO$_4$, filtered and concentrated. Methylene chloride is added to the mixture which is cooled to 0° C. for about one hour. The resulting solid is filtered and washed with cold methylene chloride. The solid is dried under vacuum at ambient temperature.

TABLE 1

Suitable amines for use in Example 18

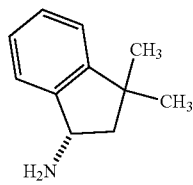
amine-i

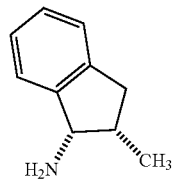
amine-ii

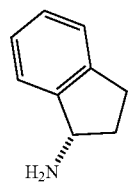
amine-iii

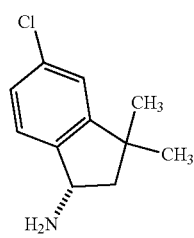
amine-iv

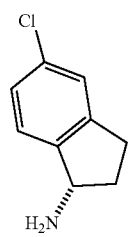 [SMILES: N[C@H]1CCc2cc(Cl)ccc21]
amine-v

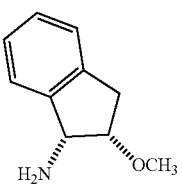 [SMILES: CO[C@H]1Cc2ccccc2[C@H]1N]
amine-vi

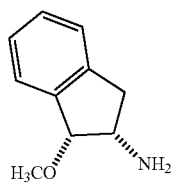
amine-vii

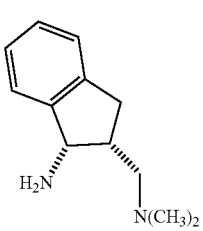 [SMILES: CN(C)C[C@H]1Cc2ccccc2[C@H]1N]
amine-viii

TABLE 1-continued

Suitable amines for use in Example 18 amine-ix, amine-x, amine-xi, amine-xii, amine-xiii, amine-xiv, amine-xv, amine-xvi, amine-xvii

Example 19: General Sulfamoylating Conditions 1

To a reaction vessel is added triethylenediamine (approximately 4 equiv. with respect to input product of Example 18) and tetrahydrofuran (approximately 12 volumes with respect to input product of Example 18). The mixture is cooled to 0° C. and 0.866 M of tert-butyl (chlorosulfonyl)carbamate (prepared by adding tert butyl alcohol to a molar equivalent of chlorosulfonyl isocyanate in the appropriate amount of anhydrous THF and stirring for about 1 hour whilst keeping the temperature below about 15° C.) in tetrahydrofuran (approximately 3 equiv. with respect to input product of Example 18) is added with cooling at such a rate that the internal temperature remains less than or equal to 15° C. The suspension is warmed to ambient temperature and stirred for about 30 minutes, then cooled to −20° C. The product from Example 18 is added in one portion followed by additional tetrahydrofuran (approximately 3 volumes with respect to input product of Example 18). The reaction mixture is warmed to 0° C. and allowed to stir until HPLC indicates that there is less than 1% by area starting material present. The reaction mixture is cooled to 0° C. and 9M hydrochloric acid in water (approximately 25 volumes with respect to input product of Example 18) is added slowly maintaining a temperature of less than 25° C. The resulting mixture is then allowed to warm to ambient temperature and stirred for about 4 hours or until such time as HPLC indicates complete BOC deprotection. On completion of deprotection, sodium bicarbonate is added portionwise until pH~8 is reached. Excess solids are filtered if a biphasic mixture is observed and the bed is washed with ethyl acetate. The organic layer is separated. The aqueous layer is extracted with ethyl acetate, all the organics are combined and washed with saturated NaCl aq., and concentrated to give a crude product which is purified by column chromatography. The product can be further purified by crystallization from an appropriate solvent.

Example 20. General Sulfamoylating Reagent Preparation 1

To a reaction vessel is added the alcohol of formula $(R^w)(R^v)_2C\text{—OH}$ (1.1 equiv) and anhydrous methylene chloride (approximately 20 volumes) and the mixture is cooled to about 0° C. to 10° C. Chlorosulfonyl isocyanate (1 equiv) is added at a rate that keeps the temperature below about 10° C. and the mixture is stirred for about 1 hour. A base (2.6 equiv.) is added portionwise whilst keeping the temperature below about 15° C. and the mixture is then stirred for about 1 hour at about 0° C. to 15° C. The solids are removed by filtration and the bed is washed with methylene chloride (approximately 5 volumes). The solvent is removed under reduced pressure and acetonitrile (approximately 5 volumes) is added to the residue and the resultant suspension is stirred at room temperature for about 3 hours. The sulfamoylating reagent is collected by filtration, washed with acetonitrile (1 volume) and dried under vacuum.

Example 21: General Sulfamoylating Conditions 2

To a reaction vessel is added the product from Example 18 (1 equiv.) and NMP (approximately 9 volumes with respect to the input product from Example 18). The mixture is cooled to between about 0° C. to 10° C. and stirred for about 15 minutes. The sulfamoylating reagent generated in Example 20 (1 equiv. with respect to input product from Example 18) and an acid (1 equiv. with respect to the input product from Example 18) is added and the mixture is stirred at a temperature of between about 0° C. to 10° C. The reaction is followed by HPLC. A further 1 equivalent portion of the sulfamoylating reagent generated in Example 20 and the acid are added approximately hourly until the reaction is complete. Water (approximately 2.5 volumes with respect to the input product from Example 18) is added and the mixture is stirred at about 15° C. for about 16 hours. Ethyl acetate (approximately 15 volumes with respect to the input product from Example 18) and water (10 volumes with respect to the input product from Example 18) are added, the resulting mixture is stirred for about 10 minutes and the resulting layers are separated. The organic phase is then washed with water (3×15 volumes with respect to the input product from Example 18). The organic phase is then dried over anhydrous sodium sulfate and the solvent is removed under reduced pressure.

The crude product is dried under vacuum before redissolving in acetonitrile (6.5 volumes with respect to the input product from Example 18). Hydrochloric acid (2.4 volumes with respect to the input product from Example 18) is added while keeping the reaction temperature below about 20° C. The reaction is followed by HPLC until removal of the protecting group is complete. Water (approximately 14 volumes with respect to the input product from Example 18) is added followed by sodium bicarbonate until a pH of 7-8 is achieved. Ethyl acetate (approximately 15 volumes with respect to the input product from Example 18) is added and after stirring for about 10 minutes the layers are separated. The organic layer is washed with water (approximately 3×15 volumes with respect to the input from Example 18) and is dried over anhydrous sodium sulfate. The solvent is removed and the residue dissolved in 7% acetonitrile in methylene chloride (approximately 11 volumes with respect to the input product from Example 18) and is stirred for about 18 hours. The product is harvested by filtration and dried under vacuum at between 30° C.–35° C.

Example 22: General Sulfamoylating Reagent Preparation 2

To a reaction vessel is added chlorosulfonyl isocyanate (1 equiv) and anhydrous toluene (approximately 20 volumes), and the mixture is cooled to about 0-10° C. Tert-butyl alcohol (1 equiv) is added at a rate to keep the reaction temperature below about 10° C., and the mixture is stirred for about 1 hour. Triethylenediamine (2 equiv.) is added portionwise whilst keeping the temperature below about 15° C., and the mixture is then stirred for about two hours at a temperature between about 15° C. to about 25° C. The sulfamoylating reagent is collected by filtration under nitrogen protection and dried under vacuum.

Example 23: General Sulfamoylating Conditions 3

To a reaction vessel is added the product from Example 18 (1 equiv.) and acetonitrile (approximately 7 volumes with respect to the input product from Example 18). The sulfamoylating reagent generated in Example 22 (2 equiv. with respect to input product from Example 18) is added and the mixture is stirred at a temperature of about 50° C. The reaction is followed by HPLC. Heating is allowed to continue until the reaction is complete. After cooling to room temperature, 0.5 N HCl (approximately 5.5 volumes with respect to the input product from Example 18) is added and the mixture is stirred at about 23° C. for about 5-6 hours. The aqueous phase is separated from the resulting biphasic solution and extracted with MTBE (approximately 5 volumes with respect to the input product from Example 18). The MTBE extract is combined with previously separated organic phase and additional MTBE (about 2 volumes with respect to the input product from Example 18) is added. The resulting mixture is stirred with water (approximately 10 volumes with respect to the input product from Example 18) for 10 minutes. The organic phase is separated. To the organic phase is added acetonitrile (approximately 10 volumes with respect to the input product from Example 18), and the solution is reduced to 10 volumes with respect to the input of product from Example 18 under reduced pressure. Additional acetonitrile (approximately 8 volumes with respect to the input of product from Example 18) is added, and again the solution is reduced to 10 volumes with respect to the input of product from Example 18 under reduced pressure.

To the crude product acetonitrile solution is added slowly, concentrated hydrochloric acid (3 volumes with respect to the input product from Example 18) while keeping the reaction temperature below about 5° C. The reaction is followed by HPLC until removal of the protecting group is complete. Water (approximately 10 volumes with respect to the input product from Example 18) is added followed by sodium bicarbonate until a pH of 7-8 is achieved. Ethyl acetate (approximately 10 volumes with respect to the input product from Example 18) is added and after stirring for about 10 minutes the layers are separated. The organic layer is washed with water (approximately 3×10 volumes with respect to the input from Example 18). Brine (about 5% v/v) is optionally added during the $2^{nd}$ and $3^{rd}$ washes to help phase separation. The crude product solution is optionally allowed to pass through a plug of activated carbon or silica gel (about 250%-25% w/w with respect to the input product from Example 18). EtOAc (about 2-10 volumes with respect to the input product from Example 18) is used to flush the activated carbon or silica gel plug. The resulting solution is concentrated to approximately 3 volumes with respect to the input product from Example 18, and then heated at 35-40° C. Dichloromethane (20 volumes with respect to the input product from Example 18) is added slowly while the internal temperature is kept at 35-40° C. After addition of DCM is complete, the suspension is stirred at 35-40° C. for 1 hour, and allowed to cool to room temperature and then stirred at room temperature for about 18 hours. The resulting solid is collected by filtration and dried under vacuum at 30-35° C. to a constant weight.

Example 24: Tert-butyl [(1R,3R,4R,5R)-4-bromo-7-oxo-6-oxabicyclo[3.2.0]hept-3-yl]carbamate To (1R,4R)-4-[(tert-butoxycarbonyl)amino]cyclopent-2-ene-1-carboxylic acid (400.00 g, 1.7601 mol; prepared in a procedure analogous to that described in Examples 1 to 3 above) dissolved in methylene chloride (6 L) was added tetrabutylammonium hydroxide in methanol (1.0M, 1800 ml), and the mixture was stirred at ambient temperature for 60 minutes. The reaction mixture was then cooled to −25° C. under a blanket of Nitrogen. Bromine (181 ml, 3.52 mol) in methylene chloride (2 L) was then added slowly over 60 minutes, maintaining an internal temperature lower than −20° C. On completion of the bromine addition, the mixture was stirred at −25° C. for a further 30 minutes, and then warmed slowly to 0° C. over 30 minutes. The mixture was then allowed to stir at 0° C. for 1 hour. At 0° C., a mixture of L-ascorbic acid sodium salt (523.0 g, 2.640 mol) in water (3 L) and saturated sodium bicarbonate in water (3 L), was added slowly over 30 minutes maintaining an internal temperature lower than 10° C. The resulting bi-phasic mixture was stirred and allowed to warm to ambient temperature over 1 hr. The methylene chloride layer was separated and the aqueous layer was extracted with methylene chloride (2 L). The methylene chloride layers were combined and concentrated to a volume of about 4 L. Ethyl acetate (8 L) was added, and the mixture was concentrated to a volume of about 5 L. Ethyl acetate (5 L) was added, and the resulting mixture was washed 3 times with water (4 L). The organic layer was then washed with saturated sodium chloride in water (2 L) and concentrated to afford the title compound (460 g, 85%) as a white solid. $^1$H NMR (300 MHz, CDCl3): δ 5.09 (d, 1H), 4.80 (m, 1H), 4.71 (m, 1H), 4.47 (m, 1H), 4.04 (m, 1H), 2.39 (m, 1H), 1.89 (m, 1H) and 1.46 (bs, 9H).

Example 25: Tert-butyl [(1R,2R,3R,4S)-2-bromo-3-hydroxy-4-(hydroxymethyl)cyclopentyl]carbamate Tert-butyl [(1R,3R,4R,5R)-4-bromo-7-oxo-6-oxabicyclo[3.2.0]hept-3-yl]carbamate (450.0 g, 1.470 mol) was dissolved in THF (6 L) and the mixture was cooled to 0° C. 2.0M lithium tetrahydroborate in THF (730 ml) was added slowly, maintaining an internal temperature lower than 10 OC. The mixture was then stirred at 0° C. for 30 minutes, after which HPLC indicated that the starting material had been consumed. At 0° C., a mixture of saturated ammonium chloride in water (2.5 L) and water (2.5 L) was added slowly, maintaining an internal temperature lower than 10° C. The mixture was then allowed to warm to ambient temperature, at which point the THF layer was separated. The THF layer was concentrated to about 2 L, and the aqueous layer was extracted twice with ethyl acetate (4 L). The organic layers were combined and washed twice with water (4 L). The organic layer was then washed with saturated sodium chloride in water (4 L) and concentrated to yield the title compound (452 g, 99%) as a yellow residue. $^1$H NMR (300 MHz, CDCl3): δ 4.83 (m, 1H), 4.54 (m, 1H), 4.43 (m, 1H), 4.31 (m, 1H), 3.87 (m, 1H), 3.74 (m, 1H), 2.71 (m, 1H), 2.02 (m, 1H), 1.70 (m, 1H) and 1.41 (bs, 9H).

Example 26: (1S,2S,4R)-4-amino-2-(hydroxymethyl)cyclopentanol.HBr

Tert-butyl [(1R,2R,3R,4S)-2-bromo-3-hydroxy-4-(hydroxymethyl)cyclopentyl]carbamate (444.0 g, 1.431 mol) was dissolved in isopropyl alcohol (2000 ml). To this solution, 4.0M hydrochloric acid in 1,4-dioxane (2000 ml) was added and the mixture was stirred at ambient temperature for 3 hours. An aliquot was concentrated and analyzed by $^1$H NMR, which indicated that the starting material had been consumed. The remaining reaction mixture was concentrated under reduced pressure at 35° C. to give a clear residue. This residue was dissolved in a mixture of methanol (2000 ml) and isopropyl alcohol (2000 ml), to which 10 weight % Pd/C (76 g, 2.5 mol %) followed by sodium bicarbonate (360 g, 4.3 mol) was added. The resulting heterogeneous mixture was subjected to hydrogen (20 psi) at ambient temperature for 18 hours. An aliquot of the reaction mixture was syringe filtered, concentrated, and analysis by $^1$H NMR indicated the complete consumption of the starting material. The remaining reaction mixture was filtered through a pad of Celite (250 g). The filter bed was washed with methanol (2000 ml) and the filtrate concentrated under reduced pressure at 35° C., to yield the title compound (310 g, quantitative) as an orange solid. $^1$H NMR (300 MHz, CD3OD): δ4.17 (t, 1H), 3.83 (m, 1H), 3.72 (m, 1H), 3.60 (m, 1H), 2.33 (m, 1H), 2.21 (m, 1H), 2.03 (m, 1H) and 1.79 (m, 2H).

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:
1. A compound of formula (Ia):

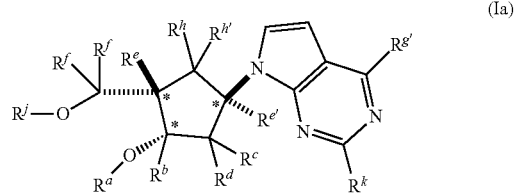

or a salt thereof; wherein:
stereochemical configurations depicted at asterisk positions indicate absolute stereochemistry;
$R^a$ is hydrogen; or $R^a$ taken together with $R^j$ and the intervening atoms forms a cyclic diol protecting group;
$R^b$ is hydrogen;
$R^c$ is hydrogen;
$R^d$ is hydrogen;
$R^e$ is hydrogen;
$R^{e'}$ is hydrogen;
each $R^f$ is independently hydrogen;
$R^{g'}$ is chloro, bromo, fluoro, or iodo;

$R^h$ is hydrogen;
$R^{h'}$ is hydrogen;
$R^j$ is hydrogen; or $R^j$ taken together with $R^a$ and the intervening atoms forms a cyclic diol protecting group;
$R^k$ is hydrogen.

2. The compound of claim 1, wherein the compound is:

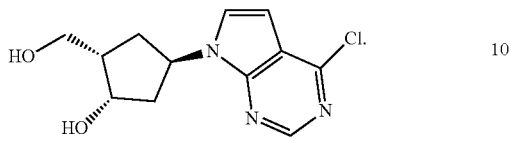

3. The compound of claim 1, wherein each of $R^a$ and $R^j$ is hydrogen.

4. The compound of claim 3, wherein $R^{g'}$ is chloro, bromo, or iodo.

5. The compound of claim 4, wherein $R^{g'}$ is chloro or bromo.

6. The compound of claim 1, wherein $R^{g'}$ is chloro, bromo, fluoro, or iodo.

7. The compound of claim 6, wherein $R^{g'}$ is chloro or bromo.

* * * * *